United States Patent [19]
Young et al.

[11] Patent Number: 6,071,476
[45] Date of Patent: Jun. 6, 2000

[54] EXHAUST GAS SENSOR

[75] Inventors: Daniel Young, Gurnee, Ill.; Jeffrey Naber, Dearborn; Neil Adams, Novi, both of Mich.; Edward Balko, Middletown, N.J.; Patrick Blosser, East Windsor, N.J.; Linda Hratko, Colonia, N.J.; Gerald Koermer, Roseland, N.J.; Jie Xue, Buffalo Grove, Ill.; Adam Moya; Chowdary Koripella, both of Albuquerque, N. Mex.

[73] Assignees: Motorola, Inc., Schaumburg, Ill.; Engelhard Corp., Iselin, N.J.

[21] Appl. No.: 08/970,259

[22] Filed: Nov. 14, 1997

[51] Int. Cl.$^7$ .................................................. G01N 25/20
[52] U.S. Cl. ............................... 422/51; 422/83; 422/94; 422/98
[58] Field of Search ................................ 422/51, 83, 98, 422/94

[56] References Cited

U.S. PATENT DOCUMENTS

| | | | |
|---|---|---|---|
| 3,932,197 | 1/1976 | Katz et al. | 136/120 FC |
| 3,979,227 | 9/1976 | Katz et al. | 427/115 |
| 4,000,006 | 12/1976 | Trocciola et al. | 427/115 |
| 4,001,042 | 1/1977 | Trocciola et al. | 427/115 |
| 4,036,592 | 7/1977 | Brown et al. | 23/232 E |
| 4,171,288 | 10/1979 | Keith et al. | 252/462 |

(List continued on next page.)

FOREIGN PATENT DOCUMENTS

| | | |
|---|---|---|
| 0 259 175 | 3/1988 | European Pat. Off. |
| 0 704 697 | 4/1996 | European Pat. Off. |
| 0 704 698 | 4/1996 | European Pat. Off. |
| 0 849 587 | 6/1998 | European Pat. Off. |
| 0 849 588 | 6/1998 | European Pat. Off. |
| WO 91/06849 | 5/1991 | WIPO. |
| WO 95/00235 | 1/1995 | WIPO. |
| WO 95/35152 | 12/1995 | WIPO. |
| WO 97/33165 | 9/1997 | WIPO. |

OTHER PUBLICATIONS

D.W. Dabill et al., "A Fast–Response Catalytic Sensor for Flammable Gases," *Sensors and Actuators*, 11:135–143 (1987).

S.J. Gentry et al., "Poison–Resistant Catalytic Flammable–Gas Sensing Elements," *Sensors and Actuators*, 5:239–251 (1984).

M. Haruta et al., "Low–Temperature Oxidation of CO Over Gold Supported on $TiO_2$, $\alpha-Fe_2O_3$, and $Co_3O_4$," *Journal of Catalysis*, 144:175–192 (1993).

(List continued on next page.)

*Primary Examiner*—Jill Warden
*Attorney, Agent, or Firm*—Marshall, O'Toole, Gerstein, Murray & Borun

[57] ABSTRACT

A differential calorimetric gas sensor (10) which includes a sensing element (12) having a catalytic layer (14) disposed on a multi-layered substrate (26). Catalytic layer (14) includes an active catalyst region (14*a*) which oxidizes total combustibles within an exhaust gas stream and a reference catalyst region (14*b*) which oxidizes selective combustibles within the exhaust gas stream. An electrochemical oxygen source (18) is disposed on an opposite side of multi-layer substrate (26) from sensing element (12). An oxygen sensor cell (170) may be incorporated into electrochemical oxygen source (18). The multi-layered substrate (26) includes a plurality of overlaying insulating layers in which an intermediate layer (60) and a bottom layer (64) support primary heaters (58, 62), and in which another intermediate layer (52) supports compensation heaters (50*a*, 50*b*). The primary heaters (58, 62) function to maintain sensor (10) at a substantially constant temperature, while the compensation heaters (50*a*, 50*b*) function to restore temperature deviations determined by temperature-sensitive elements (46*a*, 46*b*) located on an inner layer (48) overlaying the compensation heaters (50*a*, 50*b*) resulting from the catalytic reactions taking place at the surfaces (34*a*, 34*b*) of the catalyst regions (14*a*, 14*b*). The control circuitry (300) operates to control the primary heater (58, 62) and the compensation heaters (50*a*, 50*b*), as well as to minimize the response variations of the temperature-sensitive elements (46*a*, 46*b*).

124 Claims, 14 Drawing Sheets

U.S. PATENT DOCUMENTS

| | | | |
|---|---|---|---|
| 4,185,131 | 1/1980 | Goller et al. | 427/113 |
| 4,294,801 | 10/1981 | Segawa et al. | 422/98 |
| 4,329,874 | 5/1982 | Maeda | 73/190 CV |
| 4,416,911 | 11/1983 | Wilkinson-Tough | 427/12 |
| 4,571,543 | 2/1986 | Raymond et al. | 324/425 |
| 4,579,751 | 4/1986 | Forster | 427/54.1 |
| 4,597,850 | 7/1986 | Takahasi et al. | 204/426 |
| 4,604,275 | 8/1986 | Murib | 423/437 |
| 4,624,940 | 11/1986 | Wan et al. | 502/251 |
| 4,714,694 | 12/1987 | Wan et al. | 502/304 |
| 4,724,061 | 2/1988 | Nyberg | 204/412 |
| 4,727,052 | 2/1988 | Wan et al. | 502/327 |
| 4,905,652 | 3/1990 | Nakajima et al. | 123/479 |
| 4,927,517 | 5/1990 | Mizutani et al. | 204/406 |
| 5,015,461 | 5/1991 | Jacobson et al. | 423/593 |
| 5,032,248 | 7/1991 | Kanamaru et al. | 204/429 |
| 5,045,297 | 9/1991 | Bonifaz et al. | 423/437 |
| 5,057,483 | 10/1991 | Wan | 502/304 |
| 5,106,482 | 4/1992 | Milstein et al. | 204/431 |
| 5,157,204 | 10/1992 | Brown et al. | 585/850 |
| 5,177,464 | 1/1993 | Hamburg | 340/439 |
| 5,237,818 | 8/1993 | Ishii et al. | 60/274 |
| 5,250,169 | 10/1993 | Logothetis et al. | 204/424 |
| 5,265,417 | 11/1993 | Visser et al. | 60/274 |
| 5,273,779 | 12/1993 | Chen et al. | 427/123 |
| 5,296,836 | 3/1994 | Saburi et al. | 338/34 |
| 5,321,971 | 6/1994 | Hobbs et al. | 73/23.2 |
| 5,408,215 | 4/1995 | Hamburg | 340/439 |
| 5,426,934 | 6/1995 | Hunt et al. | 60/276 |
| 5,431,011 | 7/1995 | Casarella et al. | 60/274 |
| 5,431,042 | 7/1995 | Lambert et al. | 73/116 |
| 5,444,974 | 8/1995 | Beck et al. | 60/274 |
| 5,451,371 | 9/1995 | Zanini-Fisher et al. | 422/51 |
| 5,452,576 | 9/1995 | Hamburg et al. | 60/274 |
| 5,473,304 | 12/1995 | Friese et al. | 338/23 |
| 5,476,001 | 12/1995 | Hoetzel et al. | 73/23.31 |
| 5,486,336 | 1/1996 | Dalla Betta et al. | 422/90 |
| 5,490,064 | 2/1996 | Minowa et al. | 364/424.01 |
| 5,492,611 | 2/1996 | Sugama et al. | 204/415 |
| 5,492,612 | 2/1996 | Kennard, III et al. | 204/429 |
| 5,494,701 | 2/1996 | Clough et al. | 427/126.3 |
| 5,505,073 | 4/1996 | Gerblinger et al. | 73/31.05 |
| 5,505,837 | 4/1996 | Friese et al. | 204/425 |
| 5,539,638 | 7/1996 | Keeler et al. | 364/424.03 |
| 5,597,771 | 1/1997 | Hu et al. | 502/304 |
| 5,610,844 | 3/1997 | Maus et al. | 364/557 |
| 5,625,750 | 4/1997 | Puskorious et al. | 395/22 |
| 5,667,652 | 9/1997 | Liu et al. | 204/412 |
| 5,676,912 | 10/1997 | Sharma et al. | 423/213.2 |
| 5,689,059 | 11/1997 | Oh et al. | 73/23.31 |
| 5,858,306 | 1/1999 | Oh et al. | 422/51 |

OTHER PUBLICATIONS

B. Kennedy, "Structural Trends in Bi Containing Pyrochlores: The Structure of $Bi_2Rh_2O_{7-\delta}$," *Materials Research Bulletin*, vol. 32, 5:479–483 (1997).

J.M. Longo et al., "Preparation and Structure of a Pyrochlore and Perovskite in the $BiRhO_{3+x}$ System," *Materials Research Bulletin*, 7:137–146 (1972).

U.S. Application No. 08/887,483, filed Jul. 2, 1997, G. Koermer et al, entitled "Catalyst for Selective Oxidation of Carbon Monoxide and Method Using the Same" (Attorney Docket 4189).

G. Fisher et al., "The Role of Ceria in Automotive Exhaust Catalysis and OBD–II Catalyst Monitoring," *Sae Technical Paper Series*, Document No. 931034, pp. 1–7.

J. Hepburn et al., "The Relationship Between Catalyst Hydrocarbon Conversion Efficiency and Oxygen Storage Capacity," *Sae Technical Paper Series*, Document No. 920831, pp.1–7.

Krebs et al., "A low power integrated catalytic gas sensor," pp. 155–158, *Sensors and Actuators*, B13–14 (1993).

Duk–Dong Lee, "Thick–film Hydrocarbon Gas Sensors," pp. 231–235, *Sensors and Actuators*, B1 (1990).

Sommer et al, "Methane and butane concentrations in a mixture with air determined by microcalorimetric sensors and neural networks," pp. 147–152, *Sensors and Actuators*, B12 (1993).

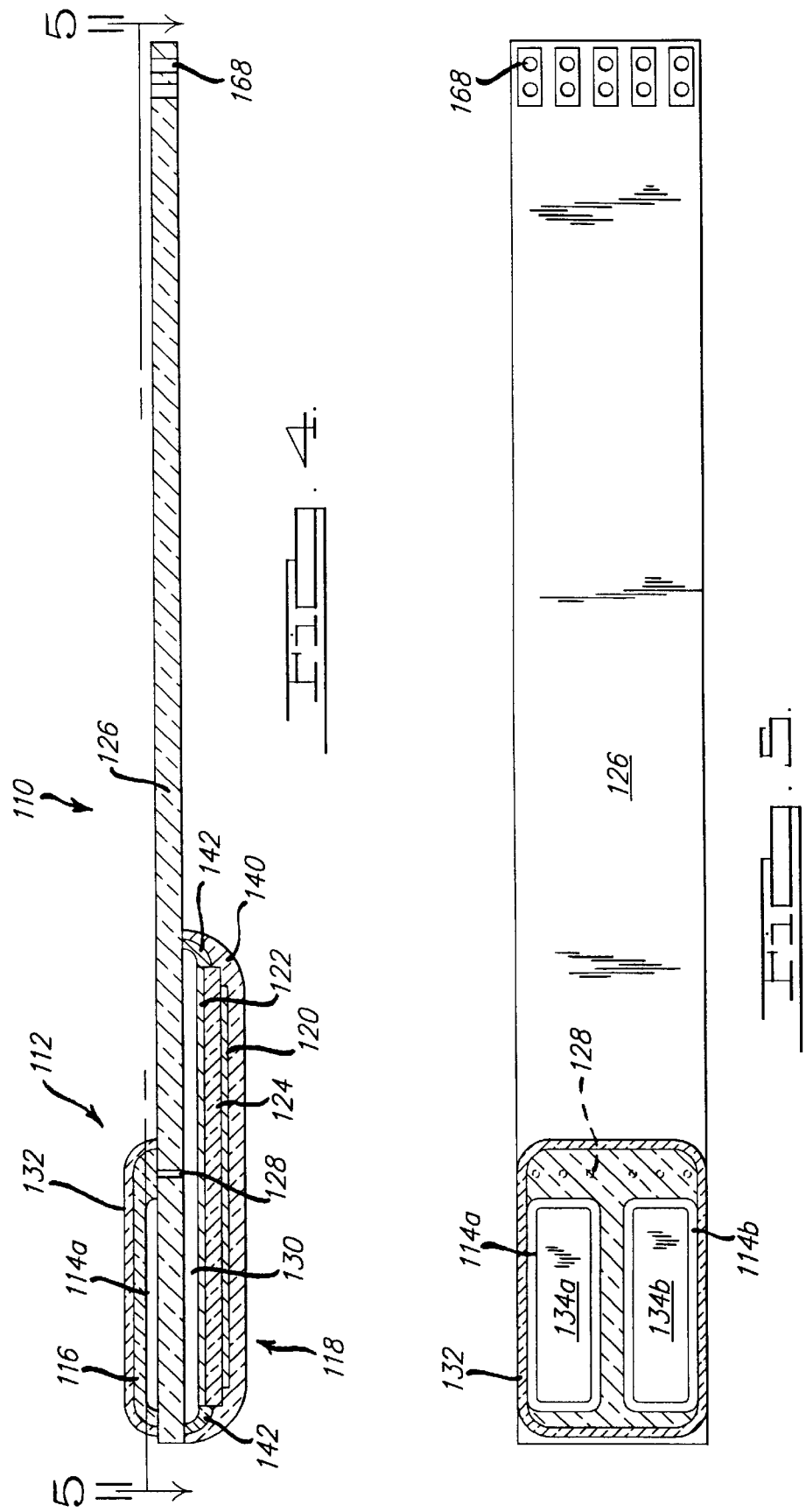

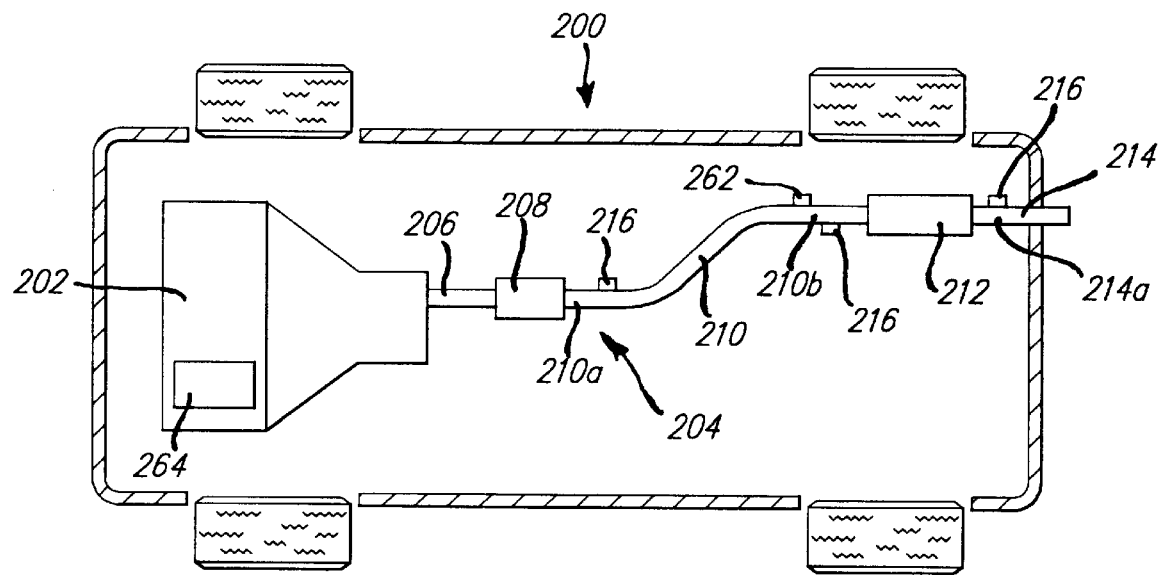
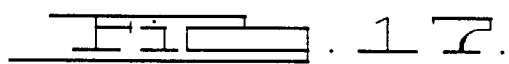
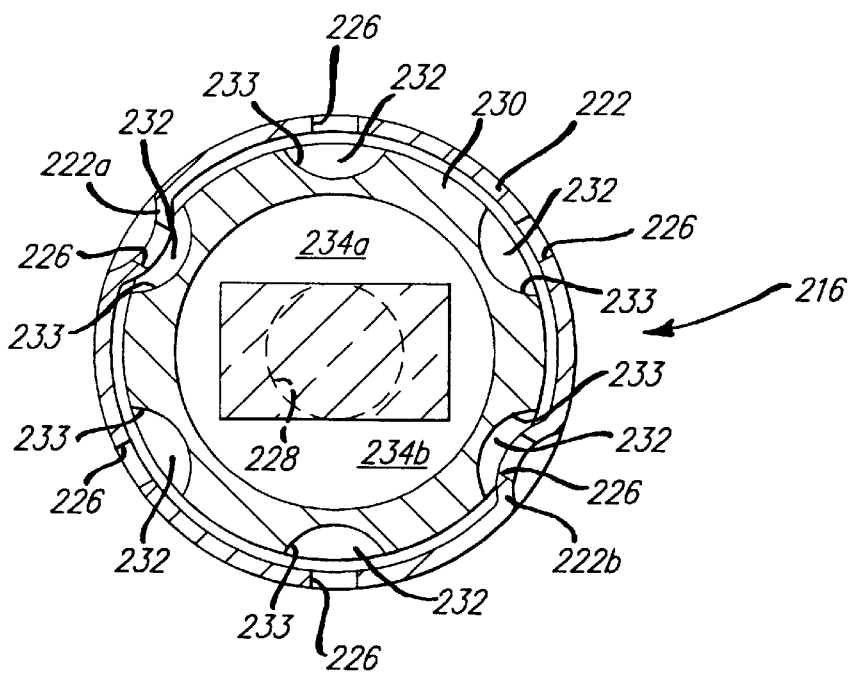
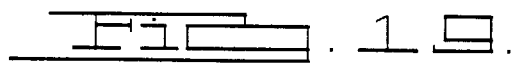

EXHAUST GAS SENSOR

CROSS-REFERENCE TO RELATED APPLICATIONS

The present application is related to the following U.S. patent applications:

| Serial No. | Filing Date | Status | U.S. Pat. No. | Patent Date |
|---|---|---|---|---|
| 08/953,871 | Oct. 20, 1997 | Patented | 5,948,683 | Sept. 7, 1999 |
| 08/887,483 | Jul. 2, 1997 | Pending | | |
| 08/970,944 | Nov. 14, 1997 | Patented | 6,019,946 | Feb. 1, 2000 |
| 08/903,524 | Jul. 30, 1997 | Patented | 5,941,918 | Aug. 24, 1999 |
| 08/963,171 | Nov. 3, 1997 | Pending | | |
| 08/970,946 | Nov. 14, 1997 | Patented | 5,956,945 | Sept. 28, 1999 |
| 08/970,940 | Nov. 14, 1997 | Patented | 6,009,742 | Jan. 4, 2000 |
| 08/970,837 | Nov. 14, 1997 | Patented | 5,989,398 | Nov. 23, 1999 |
| 08/970,698 | Nov. 14, 1997 | Patented | 6,015,533 | Jan. 18, 2000 |
| 08/970,672 | Nov. 14, 1997 | Abandoned | | |
| 08/969,882 | Nov. 14, 1997 | Abandoned | | |
| 08/970,262 | Nov. 14, 1997 | Pending | | | the disclosures of which are hereby expressly incorporated herein by reference.

FIELD OF THE INVENTION

This invention relates, in general, to gas component sensors, and more particularly, to a differential calorimetric gas sensor for the detection of certain chemical compounds present in an exhaust gas flow of an internal combustion engine.

BACKGROUND OF THE INVENTION

Sensors for the detection of particular compounds present in a high temperature gas stream find numerous applications in many different mechanical systems. For example, detection of certain compounds such as sulfur dioxide ($SO_2$), carbon monoxide (CO) and oxides of nitrogen ($NO_x$), in a high temperature gas stream is important in a variety of applications.

In automotive applications, gas sensors can be placed at various locations in an exhaust system. Exhaust gas from an internal combustion engine typically contains hydrogen ($H_2$), carbon monoxide (CO), methane ($CH_4$), carbon dioxide ($CO_2$), oxides of nitrogen ($NO_x$), water ($H_2O$), and non-methane hydrocarbons ($C_nH_m$), where n is an integer larger than 1 and m is an integer whose value depends upon the specific hydrocarbon compound, for example, alkane, alkene or aromatics. Important environmental pollution concerns dictate that the emission of hydrocarbons be minimized. To this end, catalytic converters, which convert polluting gas species such as hydrocarbon to non-polluting gas species such as carbon dioxide and water, have been incorporated into the exhaust systems of automotive vehicles to minimize pollutants from the engine exhaust. Since these converters have a finite life, legislation has been recently proposed that would require system diagnostics that evaluate the efficiency of such converters. In this regard, sensors can be placed before and after the catalytic converter to monitor the performance of the converter. Also, the emission of hydrocarbons can be controlled, in part, by an engine exhaust control system that receives a feedback signal from an exhaust sensor capable of selectively detecting the presence of certain chemical compounds in the engine exhaust.

One method for monitoring the performance of a catalytic converter includes the use of oxygen sensors within the exhaust gas system. By measuring the amount of oxygen in the exhaust gas entering and exiting a catalytic converter, an estimate of the oxygen storage capacity of the catalytic converter can be made. As the converter ages, the oxygen storing materials within the converter sinter and lose the ability to effectively store oxygen. It was commonly believed that the catalytic materials age at about the same rate as the oxygen storing materials. As the catalytic materials age the efficiency of the converter declines. Accordingly, in theory, by estimating the oxygen storage capacity of the catalytic converter, an indirect measurement of the catalytic converter efficiency can be obtained. It has been more recently shown that this method provides a rather imprecise measure of converter performance.

A sensor that directly estimates the hydrocarbon concentration in an exhaust gas stream can be used to provide a more precise determination of catalytic converter efficiency. For example, several types of sensing elements have been developed for detecting various chemical species within an exhaust gas stream. These sensing elements include calorimetric sensors having a catalyst coating, semiconductor metal oxide based sensors, and the like. Calorimetric hydrocarbon gas sensors measure the amount of heat released by the catalytic oxidation of hydrocarbons contained within the exhaust gas.

U.S. Pat. No. 5,157,204 to Brown et al. issued Oct. 20, 1992, discloses a platinum-containing catalyst for use in removing carbon monoxide and free oxygen from hydrocarbon-containing streams by contacting the stream with at least one platinum-containing catalyst composition at a reaction temperature in the range of about −30° C. to about 200° C. The catalyst compositions are said to consist essentially of platinum metal, iron oxides and an inorganic support including, among others, titania, alumina, zirconia and vanadia. Other catalyst compositions are said to consist essentially of platinum metal, palladium metal, at least one manganese compound and a tin-dioxide coated ceramic carrier. Another class of catalyst compositions is said to consist essentially of platinum metal, palladium metal, at least one manganese compound, at least one chromium compound and the tin-dioxide coated ceramic carrier.

U.S. Pat. No. 4,604,275 to Murib, issued Aug. 5, 1986, discloses a method for selectively oxidizing carbon monoxide in a hydrocarbon stream employing a supported catalyst containing cobalt oxide. The catalyst is prepared by impregnating an alumina support with an aqueous solution of a water-soluble alkaline compound whose anion is capable of forming a water-insoluble cobalt compound upon reaction with a water-soluble cobalt compound.

To obtain optimum sensitivity for the measurement of hydrocarbon species within an exhaust gas, a calorimetric hydrocarbon gas sensor must be designed to maintain a relatively constant internal temperature. This requirement is especially important given the wide temperature variations encountered in an exhaust gas system. While providing a measurement of hydrocarbon concentration, a calorimetric hydrocarbon gas sensor must be carefully designed for operation in a high temperature exhaust gas stream. For precise measurement of hydrocarbons in an exhaust gas, small temperature rises or small quantities of liberated heat must be detected when the hydrocarbons are oxidized within the sensor. Detection of these small variations can be difficult when exhaust gas temperatures are rapidly changing and subjecting the sensor to a variable temperature environment. For example, automotive engine operation is dynamic and the exhaust gas temperature varies from ambient temperature, at engine start-up to more than 1,000° C. during periods of high power operation. Thus, in calorimetric hydrocarbon gas sensor technology for applications to high temperature exhaust gas systems, a major technical challenge involves thermal management within the gas sensor.

Moreover, to obtain optimum sensitivity for the measurement of hydrocarbon species within exhaust gases, a catalytic gas sensor must have an adequate supply of oxidant to react with the relevant hydrocarbon compounds. This requirement is particularly important in exhaust gas applications which are frequently oxidant deficient.

In addition to the need to accommodate thermal variations within the exhaust gas, calorimetric sensors may require an additional source of oxidant for the catalytic oxidation of hydrocarbons. Typically, the oxidant supply system used in calorimetric hydrocarbon gas sensors must operate at elevated temperatures. High temperature operation is necessary to attain the level of efficiency needed to supply sufficient oxidant to the catalyst within the sensor. The necessity of including an oxidant supply system adds additional design constraints for a calorimetric hydrocarbon gas sensor.

Thus, improved catalytic materials, thermal management and an efficient oxidant supply system are needed within a differential calorimetric hydrocarbon gas sensor designed for the measurement of hydrocarbons in an exhaust gas stream.

BRIEF DESCRIPTION OF THE DRAWINGS

FIG. 3 is an exploded perspective view of a multi-layered substrate arranged in accordance with the invention;

FIG. 4 illustrates, in cross-section, a differential calorimetric hydrocarbon gas sensor arranged in accordance with an alternative embodiment of the invention;

FIG. 5 illustrates a cross-sectional plan view of the differential calorimetric hydrocarbon gas sensor taken along line 5—5 in FIG. 4;

FIG. 17 is an schematic illustration of a typical exhaust system for an automotive vehicle;

FIG. 19 is a cross-sectional view of the exhaust gas sensor assembly taken along line 19—19 shown in FIG. 18;

DETAILED DESCRIPTION OF THE PREFERRED EMBODIMENTS

The present invention relates to a differential calorimetric exhaust gas sensor that can be utilized in an automobile exhaust system and used to measure the concentration of chemical substances in the exhaust gas. The gas concentration measurements made by the differential calorimetric gas sensor can be converted to electrical signals and relayed to an engine control unit. Electronic circuitry within the engine control unit can analyze the electrical signals from the differential calorimetric gas sensor and determine the efficiency of certain emission control systems on the vehicle, such as the catalytic converter's efficiency at converting hydrocarbons in the exhaust gas to non-polluting gas species. The differential calorimetric gas sensor of the present invention operates by selectively oxidizing specific chemical substances within the exhaust gas stream at a catalyst surface located within the gas sensor.

With respect to the detection of hydrocarbons, the sensor utilizes selective catalysts that have catalytic activity which is restricted to certain subsets of residual combustible gases. More specifically, a first catalyst accelerates the oxidation of all residual combustible gases including specific hydrocarbons (HC) most notably non-methane HC, carbon monoxide (CO) and hydrogen ($H_2$) i.e., a "total combustible" or "TC" catalyst, and a second catalyst accelerates the oxidation of carbon monoxide (CO) and hydrogen ($H_2$) but not hydrocarbons, i.e., a "selective", "CO selective", or "COS" catalyst. These two catalysts, which differ in their catalytic activity for hydrocarbon oxidation, are used to implement a calorimetric measurement of the difference in the heat release per unit time by total oxidation of the combustibles and by selective oxidation of certain combustibles, i.e., CO and $H_2$.

The sensor also incorporates thermal measurement devices to measure the amount of heat that is released over a period of time at the catalyst surface during oxidation. To precisely determine the amount of heat released during hydrocarbon oxidation, the differential calorimetric hydrocarbon gas sensor of the invention incorporates temperature compensation circuitry to maintain the substrate and catalyst at a substantially constant operating temperature and temperature reference circuitry to measure the heat generated by the temperature compensation circuitry. Further, the functional elements of the sensor are arranged in a spaced relationship to one another, such that internal temperature uniformity is optimally maintained. Alternatively, the sensor may be operated in a free temperature rise mode.

Hydrocarbon Gas Sensor Structure

Figure 1:
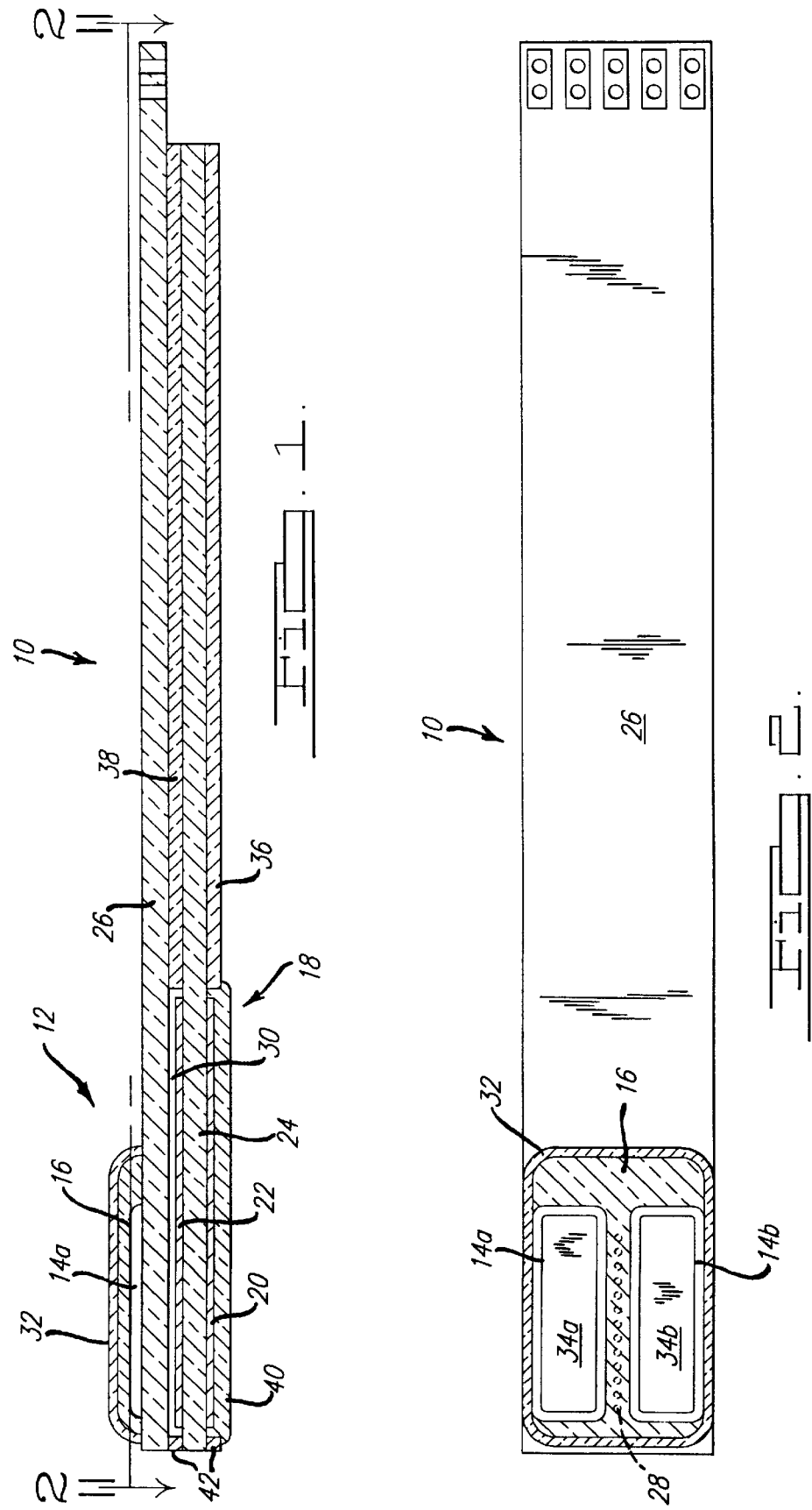
FIG. 1 illustrates, in cross-section, a differential calorimetric hydrocarbon gas sensor arranged in accordance with one embodiment of the invention.

FIG. 1 illustrates, in cross-section, a differential calorimetric hydrocarbon gas sensor 10 arranged in accordance with one embodiment of the invention. A sensing element 12 includes a catalytic layer 14, defined by catalytic layers 14a, 14b, and a transport layer 16. An electrochemical oxygen source 18 is arranged in spaced relationship with sensing element 12. Electrochemical oxygen source 18 includes an outer electrode 20 and an inner electrode 22. An electrolyte layer 24 separates the electrodes 20 and 22. Sensing element 12 is separated from electrochemical oxygen source 18 by a multi-layer substrate 26. As will subsequently be described, substrate 26 includes a plurality of overlying insulative layers on which electrical circuitry are arranged and define the temperature compensation circuitry and temperature reference circuitry. Additionally, substrate 26 includes a plurality of passageways or vias 28 extending through substrate 26. Vias 28 provide communication between transport layer 16 and an oxygen storage region 30. While shown as a plurality of apertures, vias 28 may also be formed as a slotted portion of substrate 26 or a channel extending between regions 14a and 14b. The slotted or channeled arrangement may also offer advantages of thermally isolating regions 14a and 14b. As will subsequently be described in greater detail, electrochemical oxygen source 18 and sensing element 12 are operatively disposed on opposite sides of substrate 26 in a stacked relationship such that substrate 26 regulates the temperature of both sensing element 12 and electrochemical oxygen source 18.

A diffusion barrier 32 overlies transport layer 16. Diffusion barrier 32 limits the rate at which exhaust gases diffuse to transport layer 16. Once in transport layer 16, the exhaust gases diffuse through transport layer 16 and are subsequently oxidized at an active surface 34, defined by active surface 34a and active surface 34b, of catalytic layer 14. Oxygen is transported from oxygen storage region 30 to transport layer 16 through vias 28 in sufficient quantities to permit complete oxidization of the relevant chemical compounds diffusing through diffusion barrier 32. By controlling the rate of diffusion of hydrocarbon species arriving at active surface 34, the rate of heat released by the oxidation reaction can be directly correlated with the concentration of hydrocarbons in the exhaust gases.

Those skilled in the art will recognize that the concentration of hydrocarbons at active surface 34 is not equal to the concentration of hydrocarbons in the exhaust gas at some distance therefrom. The diffusive flux of hydrocarbons from the exhaust gas to active surface 34 is a function of the difference in the concentration of hydrocarbons at active surface 34 and the concentration of hydrocarbons elsewhere in the exhaust gas. In a preferred embodiment, the concentration of hydrocarbons at active surface 34 is substantially zero. Diffusion barrier 32 so limits the diffusive flux of hydrocarbon species to active surface 34 that substantially all of the hydrocarbons are oxidized upon arrival at active surface 34. Accordingly, the diffusive flux of hydrocarbons across diffusion barrier 32 will be proportional to the hydrocarbon concentration in the exhaust gas. Moroever, the diffusion of hydrocarbon species through diffusion barrier 32 is the rate-determining step governing the transport of hydrocarbon species from the exhaust gas to active surface 34. Thus, the present invention permits a differential calorimetric measurement that accurately determines the hydrocarbon concentration in the exhaust gas by means of measuring the amount of heat released by exothermic catalytic reactions. Since all of the hydrocarbons must be completely oxidized to maintain a near-zero hydrocarbon concentration at active surface 34, the heat released by the exothermic oxidation reaction will also be proportional to the hydrocarbon concentration in the exhaust gas. Furthermore, with diffusive transport through diffusion barrier 32 largely determining the flux of hydrocarbon species arriving at active surface 34, this flux is less sensitive to other elements of the hydrocarbon transport process such as diffusion through the exhaust gas or convective transport by the exhaust gas. As a result, the proportionality constant between the heat released by exothermic oxidation and the hydrocarbon concentration in the exhaust gas is largely unaltered by variations in other transport processes.

In addition to limiting the hydrocarbon diffusive flux to active surface 34, diffusion barrier 32 also functions to protect catalytic layer 14 from scouring by particles entrained in the flowing exhaust gas. Further, by reducing heat exchange between the sensor and the environment, diffusion barrier 32 functions as a thermal barrier to limit temperature fluctuations in the heat measuring devices located in heating element 26. In the absence of diffusion barrier 32, temperature fluctuations in the exhaust gas may be transmitted to the heat measuring devices without attenuation, causing signal noise in the sensor output. The ability of diffusion barrier 32 to maintain a stable diffusion rate and to provide a suitable thermal barrier is enhanced by thermally coupling diffusion barrier 32 directly to substrate 26, and indirectly (through interface region 16) to catalytic layer 14. Preferably, diffusion barrier 32 has low-porosity and is constructed from a material, such as spinel, alumina, cordierite, mullite, steatite, stabilized zirconia or other porous ceramic. Preferably, transport layer 16 has high-porosity and is constructed from a material, such as spinel, alumina, cordierite, mullite, steatite, stabilized zirconia or other porous ceramic. Alternatively, transport layer 16 can be a gas cavity within calorimetric hydrocarbon gas sensor 10.

As presently preferred, electrochemical oxygen source 18 is a multi-layered element operatively disposed beneath substrate 26. More specifically, outer and inner ceramic layers 36 and 38 are respectively disposed on either surface of electrolyte 24, except for the regions occupied by outer and inner electrodes 20 and 22. Preferably, electrolyte 24 is yttrium stabilized zirconia, and outer and inner electrodes 20 and 22 are constructed of porous platinum metal. Placing a DC voltage across electrodes 20 and 22 generates oxygen ions by breaking down water and carbon dioxide in the exhaust gas at outer electrode 20 and conducting oxygen ions through electrolyte 24 to inner electrode 22. A porous protective layer 40 overlies outer electrode 20 and extends to ceramic layer 36. Porous protective layer 40 functions to protect outer electrode 20 from scouring by the exhaust gas, while permitting water and carbon dioxide to diffuse to outer electrode 20. Preferably, protective layer 40 has high porosity and is constructed from a material, such as spinel, alumina, cordierite, mullite, steatite, stabilized zirconia or other porous ceramic.

Oxygen is desorbed from inner electrode 22, and is contained within oxygen storage region 30. Ceramic layer 38, including end wall 42 forms the perimeter of oxygen storage region 30. Oxygen within oxygen storage region 30 is transported through vias 28 to transport layer 16. In addition to providing an oxygen supply source for catalytic oxidation of hydrocarbons at active surface 34, oxygen source 18 can be operated in reverse by reversing the polarity of the DC voltage applied across electrodes 20 and 22 to remove oxygen from transport layer 16 and oxygen storage region 30. Furthermore, oxygen source 18 can be used to break down water, oxygen and carbon dioxide at inner electrode 22. Hydrogen and carbon monoxide produced in this process are desorbed from inner electrode 22 into oxygen storage region 30 and diffuse through vias 28 into interface region 16. Oxygen is conducted across electrolyte 24 to outer electrode 20, and is desorbed into the exhaust gas. Oxygen entering interface region 16 through diffusion barrier 32 is preferentially consumed by catalyzed combustion with hydrogen and carbon monoxide, limiting hydrocarbon combustion with oxygen from that source. By removing the available oxygen, the oxidized combustion of hydrocarbons within calorimetric hydrocarbon gas sensor 10 can be effectively terminated so that differential calorimetric hydrocarbon gas sensor 10 can be calibrated after installation into an automotive exhaust gas system.

Figure 2:
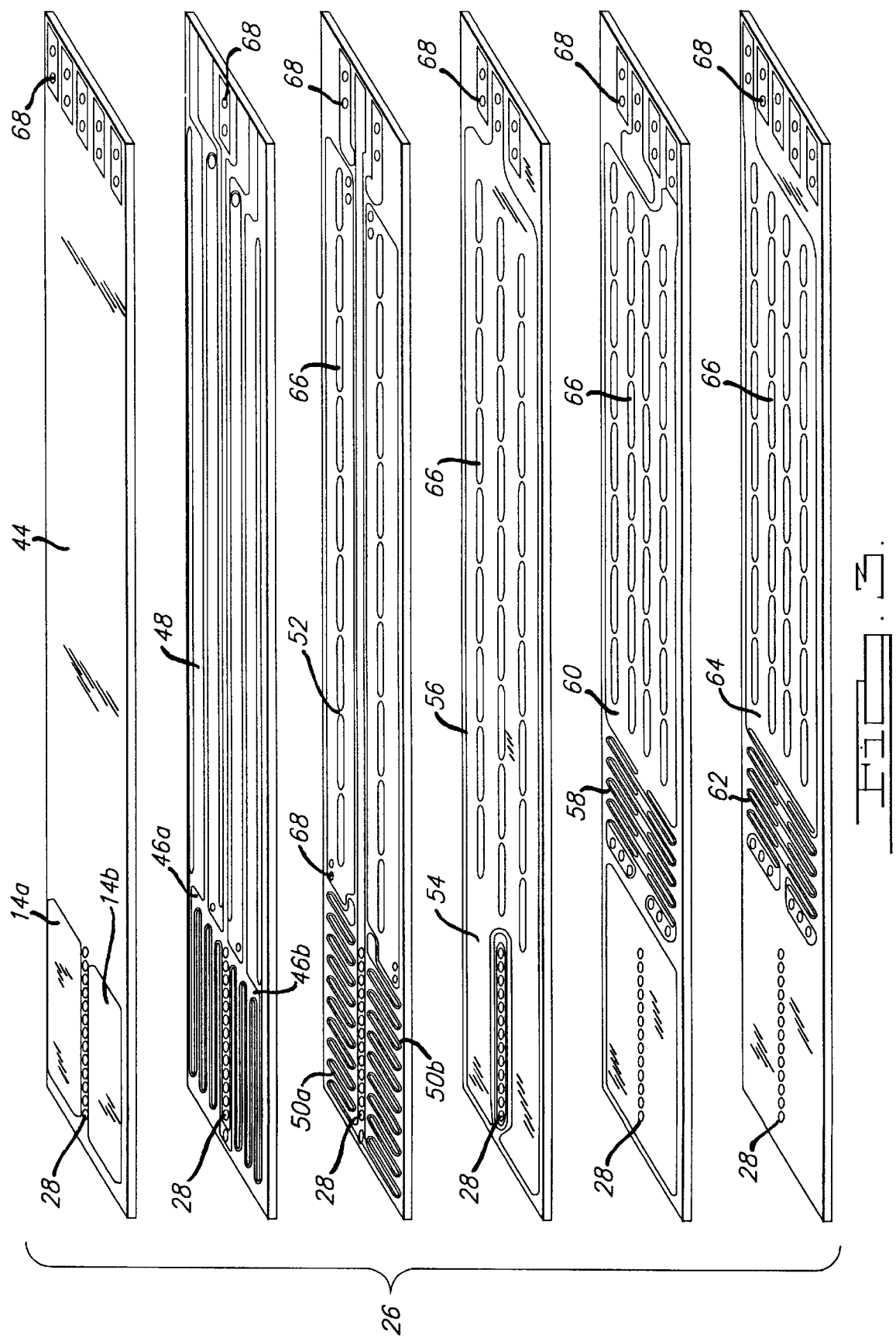
FIG. 2 illustrates a cross-sectional plan view of the differential calorimetric hydrocarbon gas sensor taken along line 2—2 in FIG. 1.

FIG. 2 shows a cross-sectional plan view of differential calorimetric hydrocarbon gas sensor 10 illustrating the arrangement of catalytic layer 34 and vias 28. Catalytic layer 34 is partitioned into an active region 14a and a reference region 14b. Active region 14a includes a catalyst composition specifically formulated to catalyze the oxidation of all relevant combustible gas species at active surface 34a. More specifically, the catalyst in active region 14a accelerates the oxidation of substantially all non-methane hydrocarbons, carbon monoxide and hydrogen. Reference region 14b includes a catalyst composition specifically formulated to catalyze the oxidation of selective gas species at reference surface 34b. More specifically, the catalyst in reference region 14b accelerates the oxidation of carbon monoxide (CO) and hydrogen ($H_2$) but not hydrocarbons. By utilizing active region 14a and reference region 14b in catalyst layer 34 which differ in their catalytic activity for hydrocarbon oxidation, it is possible to implement a differential calorimetric measurement of the differences in the heat released by the catalyzed oxidation of hydrocarbons on reference region 14b and on active region 14a. More specifically, the exothermic reaction heat measured by heat sensing circuitry 300 shown in FIG. 20 for reactions taking place at active surface 34a can be compared with the exothermic reaction heat measured by heat sensing circuitry 300 for reactions taking place at reference surface 34b. The difference in the amount of heat produced between active region 14a and reference region 14b can be attributable to the oxidation of specific hydrocarbon species within the exhaust gas.

With reference to FIG. 3, an exploded perspective view of substrate 26 is illustrated showing a plurality of overlying insulative layers that are laminated together to form a multi-layered substrate 26. In a preferred embodiment, each of the plurality of overlying insulative layers are ceramic layers laminated together to form a multi-layered ceramic substrate. Multi-layer green tape technology provides a capable and economic, and thus preferred, process for production of substrate 26. With the exception of top layer 44, each ceramic layer supports screen-printed metalization arranged in different patterns to define the various functional elements necessary to measure the heat and control the temperature within differential calorimetric hydrocarbon gas sensor 10.

More specifically, temperature reference circuitry includes temperature-sensitive elements 46a, 46b such as resistive temperature detectors (RTDs) or thermocouples that overlie intermediate layer 48. Temperature-sensitive elements 46a, 46b reside directly below active region 14a and reference region 14b, respectively, and function to measure the temperature during oxidation of combustibles at active and reference regions 14a, 14b disposed on the surface of top layer 44. The temperature compensation circuitry, which includes heat-generating elements 50a, 50b such as resistive compensation heaters disposed on the surface of intermediate layer 52 directly below temperature-sensitive elements 46a, 46b, respectively, maintains substrate 26 and catalytic layer 14 at a substantially constant operating temperature. Thus, gas sensor 10 can be conceptually thought of including a pair of calorimeters; the active calorimeter or calorimeter A including active surface 34a, temperature-sensitive element 46a and compensation heater 50a and the reference calorimeter or calorimeter B including reference surface 34b, temperature-sensitive element 46b and compensation heater 50b.

Multi-layered substrate 26 further includes a first primary heater 58 located on intermediate layer 60, and a second primary heater 62 located on bottom layer 64 below first primary heater 58. Primary heaters 58, 62 are intended to supply the highly variable and often large quantities of heat needed to maintain calorimeter A and calorimeter B within a specified temperature range. Electrical ground plane 54 defined by a metalized layer overlies intermediate layer 56 and electrically isolates compensation heaters 50a, 50b from a first primary heater 58 and second primary heater 62.

In addition to the various ceramic layers shown in FIG. 3, substrate 26 can include additional layers to promote the mechanical strength and optimize the thermal conductance of substrate 26. Importantly, the metallization overlying intermediate layers 56 and 60, and bottom layer 64 includes a plurality of slots 66 which function to promote adhesive bonding within substrate 26.

In general, substrate 26 is fabricated by first forming electrical vias 68 in each layer of green tape and filling the vias with metal, followed by screen-printing metallization onto individual layers of ceramic green tape. Vias 68 provide access to the respective metalized layers to establish electrical communication between the various layers of substrate 26, while slots 66 function to promote bonding between ceramic layers of substrate 26. Additionally, vias 68 provide access to the respective metalized layers to attach lead wires to substrate 26 for communication between differential calorimetric hydrocarbon gas sensor 10 and external electronic circuitry 300 which control sensor 10. After the individual ceramic green tape layers have been screen printed with the appropriate metallizations, multi-layer substrate 26 is assembled and fired. After cooling, catalytic layer 14 including active region 14a and reference region 14b is deposited on top layer 44 and fired.

An alternative embodiment of the invention is illustrated, in cross-section, in FIGS. 4–5. Reference numerals incremented by a factor of one hundred (100) have been used to indicate elements in FIGS. 4–5 that most closely corresponds to elements illustrated in FIGS. 1–2. Differential calorimetric hydrocarbon gas sensor 110 includes a catalytic layer 114 defined by catalytic layers 114a, 114b and having catalytic surfaces 134a, 134b formed thereon, encased within a low-porosity diffusion barrier 132 and separated therefrom by a high-porosity transport layer 116. Catalytic layer 114 overlies a multi-layer substrate 126. An oxygen source 118 resides below substrate 126 generally opposite from catalytic layer 114. Oxygen source 118 includes a zirconia electrolyte layer 124 and porous platinum electrodes 120, 122. Oxygen source 118 is separated from substrate 126 by an oxygen storage region 130. Areas of oxygen storage region 130 not in contact with platinum electrode 122 are covered by an impermeable layer 142. Oxygen source 118 and oxygen storage region 130 are encased within a porous protective layer 140. In comparison with the previous embodiment, the oxygen source of the embodiment illustrated in FIG. 4 includes a less extensive zirconia electrolyte layer. By restricting the longitudinal extent of the oxygen source, more precise thermal management is possible within the differential calorimetric hydrocarbon gas sensor.

A cross-sectional plan view of calorimetric hydrocarbon gas sensor 110 is shown in FIG. 5. A plurality of vias 128 extend through substrate 126 and connect transport layer 116 and oxygen storage region 130. In a manner analogous to the previous embodiment, vias 128 provide a diffusion pathway for oxygen produced by oxygen source 118 to diffuse through substrate 126. In contrast with the previous embodiment, vias 128 are aligned adjacent to low-porosity diffusion barrier 132. By comparing FIGS. 2 and 5 it becomes apparent that the invention contemplates the formation of vias in the substrate in a variety of geometric configurations. Additionally, it is contemplated that the vias be open, or alternatively that they be filled with a porous material.

Catalytic oxidation of total combustibles of the exhaust gas, including hydrocarbons, is carried out in active region 114a, while oxidation of selective combustibles of the exhaust gas, excluding hydrocarbons, occurs at reference region 114b. A plurality of vias 168 provide electrical connection to the various layers within substrate 126, as well as providing access to the respective metalized layers to attach lead wires to substrate 126 for communication between differential calorimetric hydrocarbon gas sensor 110 and external electronic circuitry (not shown).

Catalytic Compositions

As described above, the present invention employs two different catalysts within catalytic layer 14: a total combustible catalyst or active region 14a and a CO selective catalyst or reference region 14b. Active region 14a is a stable, high-activity catalyst composition which, at suitable oxidizing conditions and temperatures, will completely convert all residual combustible gases such as non-methane hydrocarbons, carbon monoxide, an d hydrogen to carbon dioxide and water. The composition of active region 14a is designed to provide complete combustion of substantially all residual combustible gases, at temperatures greater than approximately 450° C. when a sufficient concentration of oxidizing agent, such as oxygen or air or other oxidizing material, is present. The chemical and physical properties of active region 14a are able to withstand the operational environments of the automotive exhaust gas.

The catalyst composition for active region 14a comprises active metal components such as one or more of the following elements: platinum, rhodium, palladium, iridium, and ruthenium. Generally, platinum, rhodium and palladium are preferred. Combinations of platinum and rhodium are even more preferred. These active metals are preferably supported on a stable refractory support such as alumina, zirconia, titania, silica, silica alumina or other similar ceramic materials. High surface area materials such as gamma alumina are preferred. Optionally, an oxygen storage material such as ceria may be added to the catalyst formulation. However, this material is not essential for utility in a sensor where there is sufficient oxidizing agent present in the environment or where an oxidizing agent, such as air or oxygen, is provided by external means. Thus, even more preferred are refractory materials that are especially stabilized by thermal, geothermal or chemical means, such as precalcined alumina and ceria stabilized zirconia, a disclosure of which is provided in U.S. Pat. No. 5,057,483 entitled "Catalyst Composition Containing Segregated Platinum and Rhodium Components" issued Oct. 15, 1991 to C. Z. Wan and assigned to Engelhard, the disclosure of which is expressly incorporated by reference herein.

The particle size of the catalyst should be such that a binder can be used to adhere the catalyst formulation to substrate 26 of sensor 10. In addition, the particle size and uniformity of the catalyst should be such that the processes for catalyst deposition, such as screen printing, are feasible. In general, the mean particle size of the catalyst material should be less than ten microns in diameter with a more or less normal distribution about that mean. More preferred is a mean particle size of approximately 5 microns in diameter. Specific examples of presently preferred catalyst compositions for active region 14a are set forth below.

EXAMPLE 1

Platinum Rhodium Catalyst on Prestabilized Alumina 100 g of gamma alumina is calcined in a furnace at 850° C. for thirty minutes. 50 g of the calcined alumina is then impregnated to incipient wetness with 14.4 g of an aqueous solution (18.0% Pt) of a platinum amine hydroxide salt diluted with 11 g of water. Then 1.5 ml of acetic acid is mixed into the impregnated alumina. The remaining 50 g of calcined alumina is impregnated with 0.2 g of rhodium nitrate solution (10.37% Rh) diluted with 20 g of water. Then 1.3 ml of monoethanolamine is mixed into the rhodium impregnated alumina. Both impregnated aluminas are placed into a jar mill and then enough water is added to give a slurry of about 40% solids. Grinding media is added and the slurry is milled until a median particle size of about 5 microns is obtained. The slurry is removed from the jar and the water is removed using a rotary evaporator. The remaining solids are dried at 120° C. The catalyst can be calcined at 550° C. in preparation for deposition onto a sensor.

Figure 6:
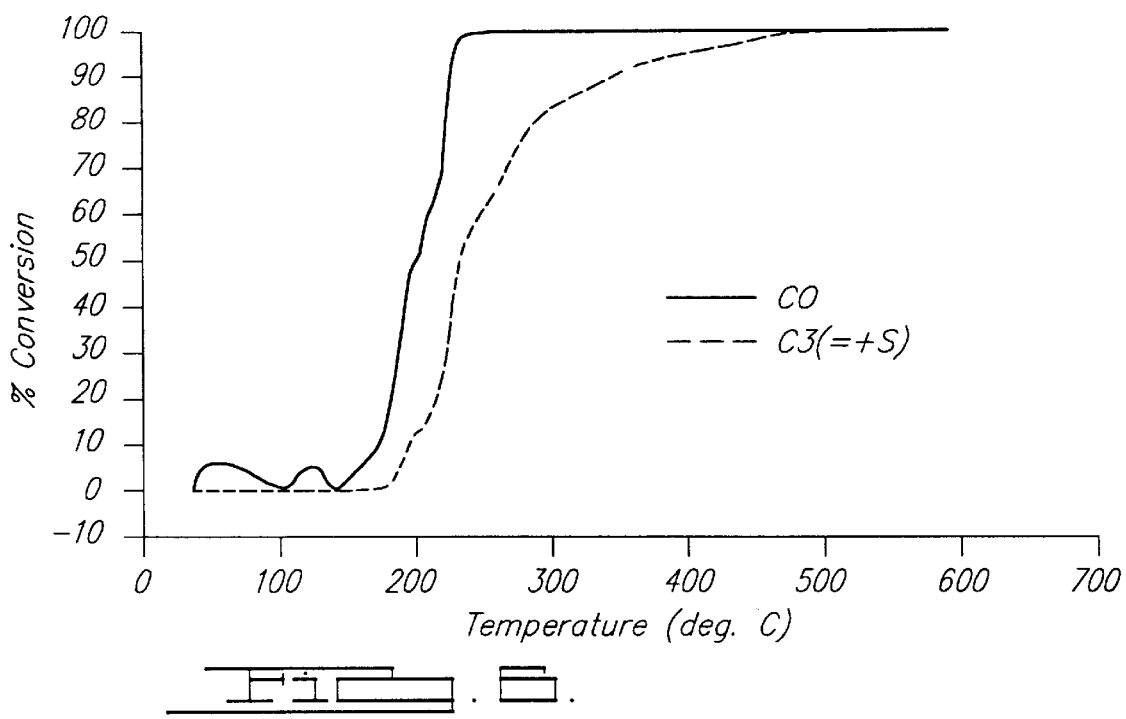
FIG. 6 is an exemplary plot which graphically illustrates the catalytic evaluation of the total combustible catalyst set forth below in example 1 for the percent conversion of carbon monoxide and propane and propylene as a function of temperature.

Catalytic evaluation of this material is shown in FIG. 6. As can be seen from the figure, the catalyst of Example 1 converts substantially all hydrocarbon and carbon monoxide species above 400° C.

EXAMPLE 2

Platinum Rhodium Catalyst on Alumina Also Containing Ceria 8.64 g of an aqueous solution (10.54% Pt) of a platinum amine hydroxide salt is diluted with 15 g water. This solution is impregnated into 123.6 g of gamma alumina (calcined 850° C. or uncalcined, calcined is preferred). 3.7 ml of acetic acid is mixed into the impregnated alumina. 1.5 g of the above aqueous Pt salt solution is diluted with 26.3 g water. This diluted solution is impregnated onto 92.8 g of ceria stabilized zirconia. 2.8 ml of acetic acid is mixed into the impregnated ceria zirconia. Both impregnated supports are placed into a mill jar along with 187 ml water and grinding media. The resulting slurry is milled for 20 minutes. 18.5 g of an aqueous rhodium nitrate solution (10.08% Rh) is diluted with 43.3 g water. This solution is impregnated into 123.6 g of alumina (calcined 850° C. or uncalcined, calcined preferred). 4.5 g of monoethanolamine is mixed into the impregnated alumina. This material is added to the mill jar containing the previously prepared slurry. The mixture is milled for approximately three (3) hours. Then 35 g of zirconium hydroxide (27.7% solids) and 2 drops of defoamer are added to the jar with an additional amount of water to thin out the slurry. The milling is continued until the medium particle size is about 5 microns. The slurry is removed from the milling jar and the water is removed using a rotary evaporator. The remaining solids are dried at 120° C. The catalyst can be calcined at 550° C. in preparation for deposition onto a sensor.

Figure 7:
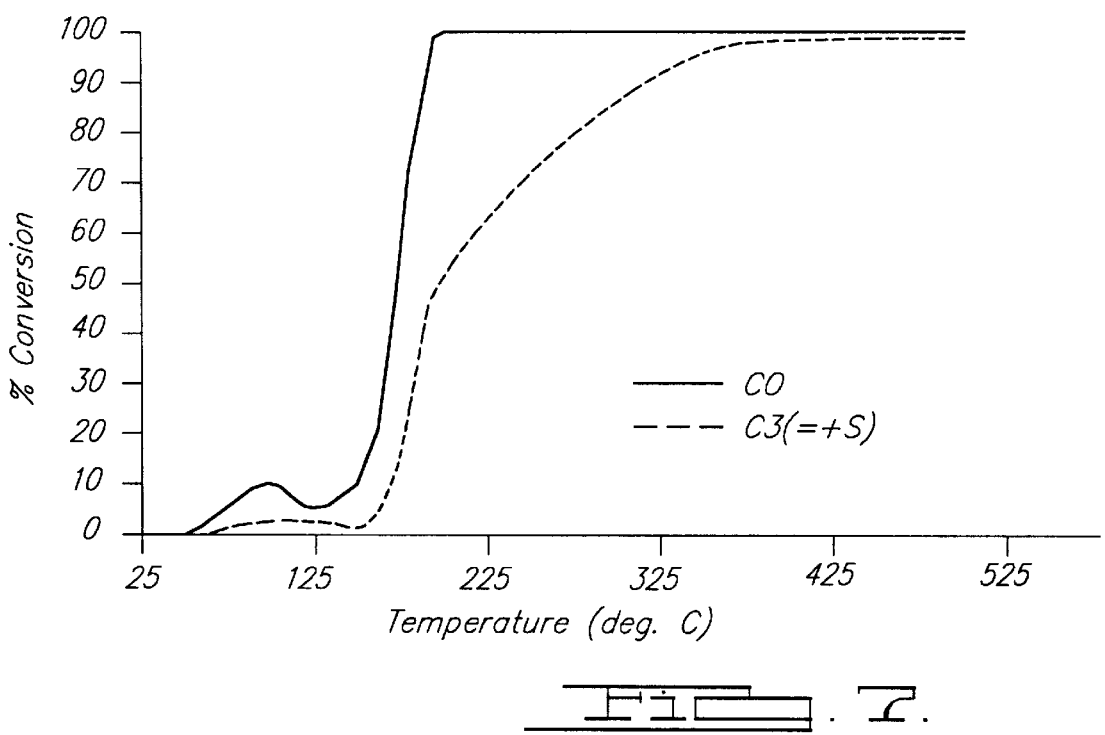
FIG. 7 is an exemplary plot which graphically illustrates the catalytic evaluation of the total combustible catalyst set forth below in example 2 for the percent conversion of carbon monoxide and propane and propylene as a function of temperature.

Catalytic evaluation of this material is shown in FIG. 7. As can be seen from the figure, the catalyst of Example 2 converts substantially all hydrocarbon and carbon monoxide species above 400° C.

EXAMPLE 3

Rhodium on Stabilized Ceria Zirconia 10 g of ceria stabilized zirconia is impregnated with 10.8 g of an aqueous rhodium nitrate solution (10.08% Rh). The ceria zirconia has a median particle size of 1.0 micron diameter with 90% less than 3.9 microns. The impregnated solids are dried in an oven at 120° C. To the dried powder is added 4.3 g of zirconium hydroxide (37% solids). To the resulting mixture is added enough water to make a slurry of 40–50% solids. The slurry is ball milled for approximately forty-five (45) minutes. Water is removed from the slurry using a rotary evaporator. The resulting solids are dried at 120° C. The catalyst can be calcined at 550° C. in preparation for deposition onto a sensor.

Figure 8:
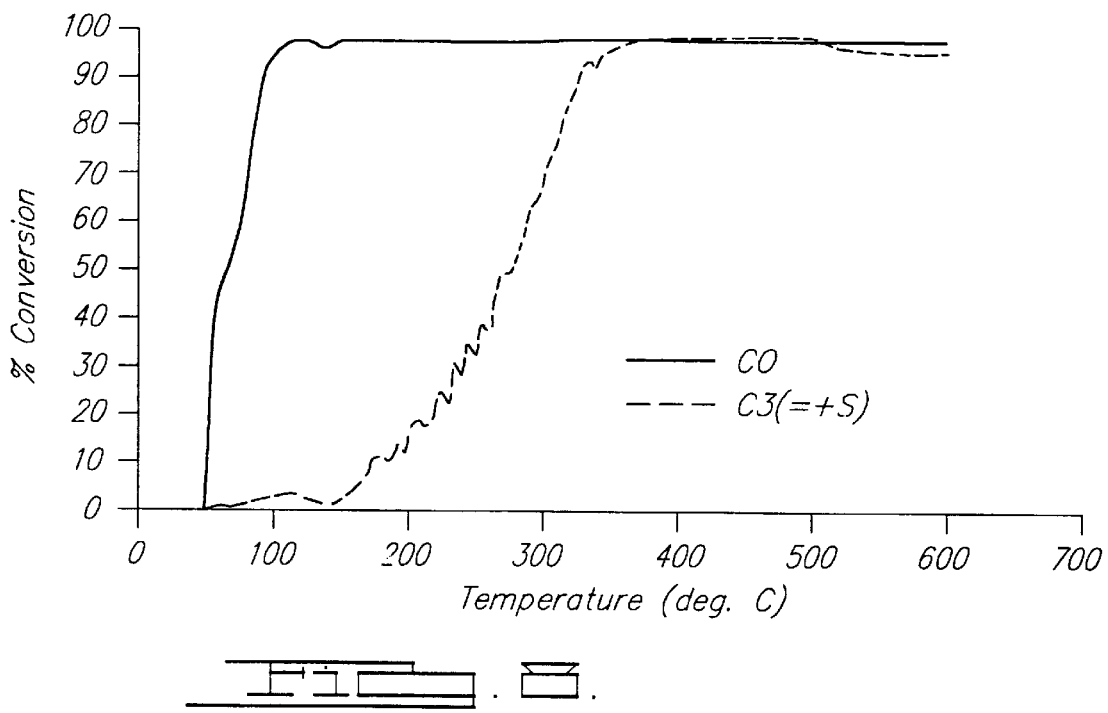
FIG. 8 is an exemplary plot which graphically illustrates the catalytic evaluation of the total combustible catalyst set forth below in example 3 for the percent conversion of carbon monoxide and propane and propylene as a function of temperature.

Catalytic evaluation of this material is shown in FIG. 8. As seen in the figure, the catalyst of Example 3 converts substantially all hydrocarbon and carbon monoxide species above 350° C.

With respect to reference region 14b the reactivity towards catalytic oxidation decreases as follows—carbon monoxide (CO)>olefins>aromatics>paraffins. As a practical matter, at elevated temperatures (greater than 200° C.), the reactivity of CO and olefins towards catalytic oxidation is similar. This means that for most catalytic systems at the temperature where oxidation of CO occurs, the oxidation of hydrocarbons (HC), particularly olefins, occurs at the same or only slightly higher temperatures than CO. In other words, the light off curves for CO and HC are relatively close together. While there are some known selective catalysts that exhibit good low temperature (less than 200° C.) oxidation activity for CO, these catalysts are not useful for applications where higher temperatures are necessary. Moreover, these catalysts tend to be easily poisoned or lose their low temperature activity for CO oxidation after exposure to elevated temperatures.

As presently preferred, reference region 14b includes a catalyst composition having a rhodium component and a bismuth component on a refractory oxide support. The rhodium and bismuth are combined as a solution of soluble salts, e.g., nitrates, sulfates, etc., at very low pH so that bismuth sub-oxide does not precipitate from the solution. Alternately, any method that intimately contacts the rhodium and bismuth can be used to synthesize the catalyst. This includes but is not limited to the inclusion of materials such as fluxes and low melting frits. The atomic ratio of bismuth to rhodium can vary over a wide range but the preferred ratio is in the range of 0.5–3.0. The most preferred ratio tends to be 1.0 to 2.5 depending on the exact materials and the exact procedure used to synthesize the catalyst.

A solution of the bismuth and rhodium salts is impregnated onto a refractory support such as zirconia or ceria stabilized zirconia. Other supports are suitable in this application, but may affect the selectivity of the catalyst under certain circumstances. For example, the selectivity of a catalyst prepared using high surface area alumina is believed to be inferior to a catalyst prepared using ceria stabilized zirconia.

Following impregnation of the refractory support with the rhodium/bismuth solution, the catalyst is dried and then calcined at a sufficiently high temperature for obtaining optimal performance. As presently preferred, calcination of the catalyst should be carried out at 850° C. for approximately ten (10) minutes. While it is likely that these time and temperature parameters can be varied significantly without affecting the performance of reference catalyst 14b, it is believed that calcination at a temperature less than 550° C. gives inferior results. An alternative preferred method of forming a catalyst layer having rhodium and bismuth components is disclosed and described in the aforementioned United States Patent Application entitled "Catalyst Structure and Method of Making Same," docket no. IR-4313e.

The resulting catalyst powder is typically coated on a small ceramic honeycomb monolith for catalytic evaluation. More specifically, approximately 4.0 grams of catalyst is combined with sufficient water to make a 45% solid slurry. The resulting slurry is homogenized with a magnetic stirrer. The slurry is transferred to a 30 ml plastic vial fitted with a snap cap. A weighed ceramic monolith in the shape of a cylinder having dimensions approximately 25 mm high by 19 mm diameter and a cell density of approximately sixty (60) cells per $cm^2$ is placed into the plastic vial. The vial is inverted several times to ensure that slurry passes through all the monolith channels. The monolith is removed from the vial and excess slurry is removed with an air knife. The monolith is weighed to determine if the appropriate amount of coating has been applied. After the coating is acceptable, the monolith is dried at 120° C. Then the monolith is placed in a crucible and the crucible is placed into a furnace. The temperature of the furnace is raised to 550° C. and held at that temperature for approximately ten (10) minutes. For certain catalysts, it may be desirable to raise the temperature of the furnace to approximately 850° C. for a period of ten (10) minutes. The crucible is removed from the furnace and cooled to room temperature. The monolith is weighed to determine the weight of the dry coating by subtracting the weight of the uncoated monolith from the weight of the coated monolith. Typical catalyst coatings on the monolith are approximately 0.6 grams with a density of approximately 0.2 grams per $cm^3$ of monolith.

Rhodium is the presently preferred metal for the catalyst in reference region 14b. While platinum, palladium or iridium may be substituted for rhodium in the standard catalytic preparation, it is believed that such combinations would necessarily require optimization for these other elements. Furthermore, it is anticipated that other modifiers for rhodium, besides or in addition to bismuth, may be added to the catalyst composition. Specific examples of presently preferred catalyst compositions for reference region 14b are set forth below.

EXAMPLE 4
Rhodium Bismuth on Ceria Zirconia

A catalyst containing rhodium and bismuth on ceria zirconia is prepared in accordance to the following procedure. 36.6 g of bismuth nitrate pentahydrate is dissolved into 58.0 g of rhodium nitrate solution (10.37% Rh). This precious metal solution is slowly added to 40.0 g ceria stabilized zirconia and stirred until incipient wetness is achieved which may not require all of the precious metal solution. This impregnated material is then dried at approximately 120° C. As needed, the previous two steps are repeated until all of the precious metal solution has been used. The impregnated material is slurried to approximately 50% solids in water. 2.4 g of zirconium hydroxide paste (50% solids) are added to the slurry and the mixture is placed into a jar with a suitable grinding media and milled until a median particle size of approximately 5 microns is achieved. A rotary evaporator removes water from the slurry which is subsequently oven dried at 120° C. 4.0 g of catalyst is slurried to 45% solid with water in preparation for coating onto a monolith using the coating procedure described above.

Figure 9:
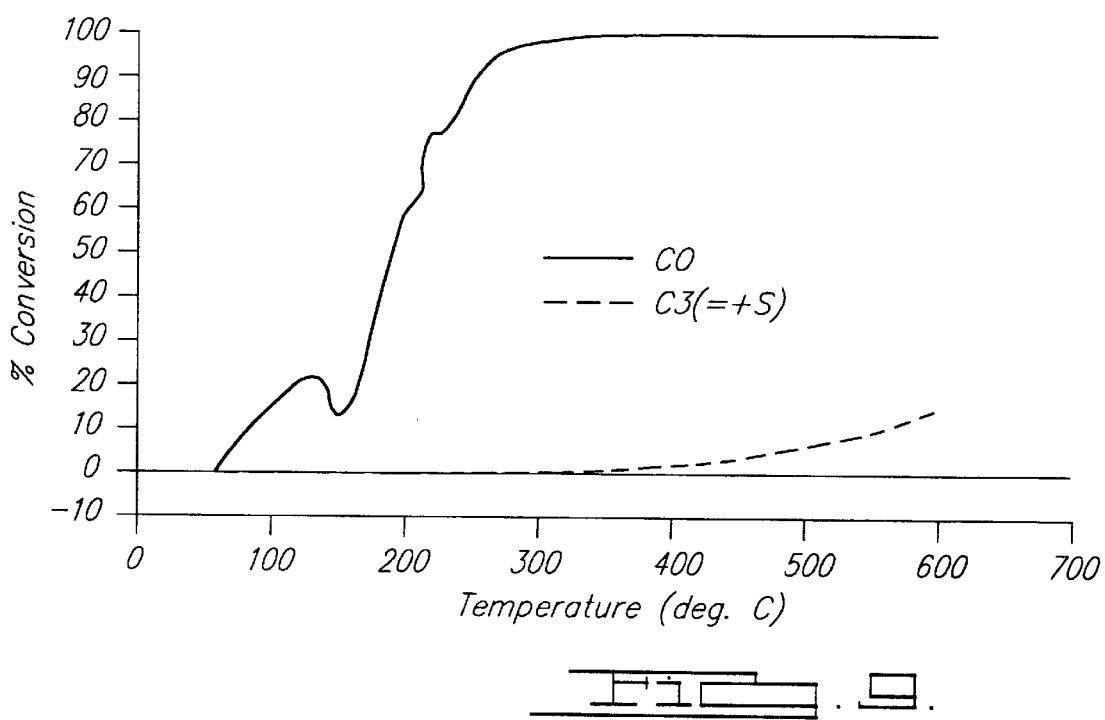
FIG. 9 is an exemplary plot which graphically illustrates the catalytic evaluation of the CO selective combustible catalyst set forth below in example 4 for the percent conversion of carbon monoxide and propane and propylene as a function of temperature.

Catalytic evaluation of this material is shown in FIG. 9. As can be seen in FIG. 9, this catalyst is very selective for carbon monoxide oxidation in the presence of hydrocarbons over a wide temperature range.

EXAMPLE 5
Rhodium Bismuth on Ceria Zirconia

A catalyst containing rhodium and bismuth on ceria zirconia is prepared in accordance to the following procedure. 6.7 g of bismuth nitrate pentahydrate is dissolved into 10.8 g of rhodium nitrate solution (10.8% Rh). This precious metal solution is slowly added to 20.0 g ceria stabilized zirconia and stirred until incipient wetness is achieved which may not require all of the precious metal solution. This impregnated material is then dried at approximately 120° C. As needed, the previous two steps are repeated until all of the precious metal solution has been used. The impregnated material is slurried to approximately 50% solids in water. 2.2 g of zirconium hydroxide paste (27% solids) are added to the slurry and the mixture is placed into a jar with a suitable grinding media and milled until a median particle size of approximately 5 microns is achieved. A rotary evaporator removes water from the slurry which is subsequently oven dried at 120° C. 4.0 g of catalyst is slurried to 45% solid with water and coated onto a monolith using the process described above with the following exceptions. The catalyst is calcined at 850° C. for ten (10) minutes.

For purposes of aging the coating, the catalyst is steamed at 700° C. for approximately twenty-four (24) hours in an atmosphere of 12% steam-88% air.

Figure 10:
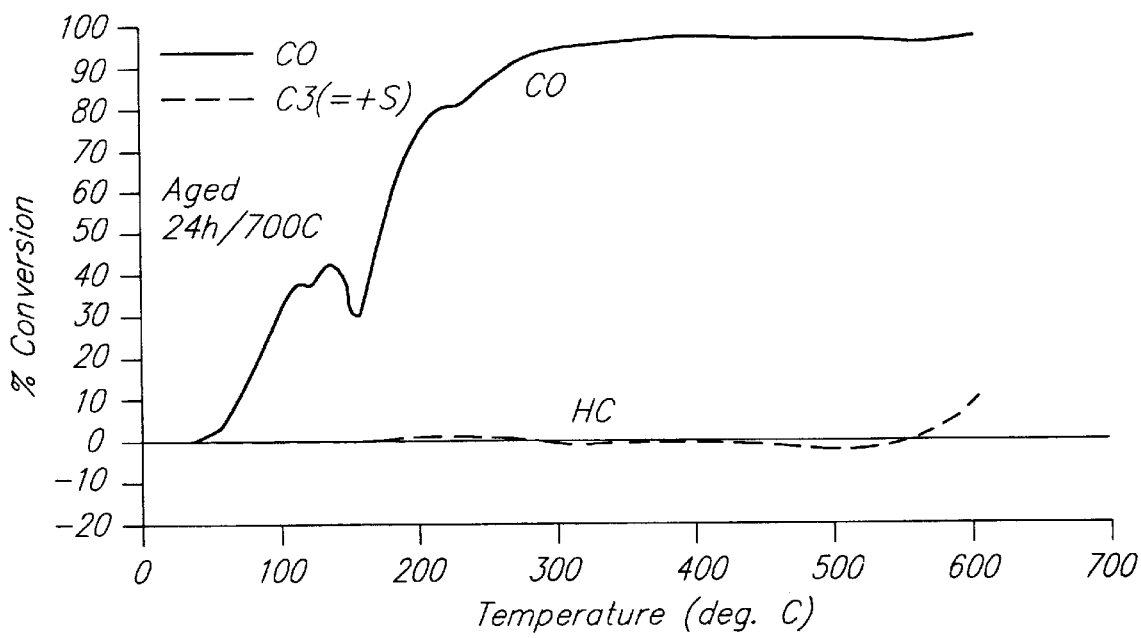
FIG. 10 is an exemplary plot which graphically illustrates the catalytic evaluation of the CO selective combustible catalyst set forth below in example 5 for the percent conversion of carbon monoxide and propane and propylene as a function of temperature.

Catalytic evaluation of this material is shown in FIG. 10. As can be seen in the figure, this catalyst is very selective for carbon monoxide oxidation in the presence of hydrocarbons. Moreover, high temperature hydrothermal aging did not deteriorate this performance.

EXAMPLE 6
Rhodium Bismuth on Zirconia

A catalyst containing rhodium and bismuth on zirconia is prepared in accordance to the following procedure. 7.6 g of bismuth nitrate pentahydrate is dissolved into 12.8 g of rhodium nitrate solution (9.75% Rh). This precious metal solution is slowly added to 20.0 g zirconium oxide (made by calcining zirconium hydroxide for approximately one (1) hour at 450° C.) and stirred until incipient wetness is achieved which may not require all of the precious metal solution. This impregnated material is then dried at approximately 120° C. As needed, the previous two steps are repeated until all of the precious metal solution has been used. The impregnated material is slurried to approximately 50% solids in water and placed into a jar with a suitable grinding media and milled until a median particle size of approximately 5 microns is achieved. A rotary evaporator removes water from the slurry which is subsequently oven dried at 120° C. 4.0 g of catalyst is slurried to 45% solid with water and coated onto a monolith using the process described above.

Figure 11:
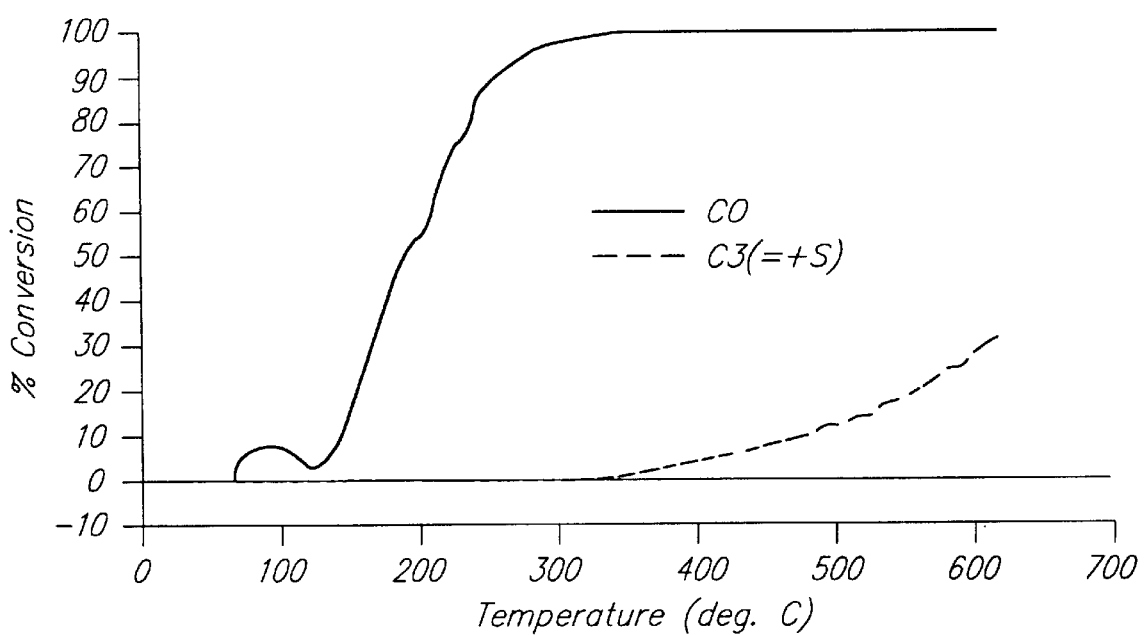
FIG. 11 is an exemplary plot which graphically illustrates the catalytic evaluation of the CO selective combustible catalyst set forth below in example 6 for the percent conversion of carbon monoxide and propane and propylene as a function of temperature.

Catalytic evaluation of this material is shown in FIG. 11. As can be seen from FIG. 11, the selectivity of this catalyst for carbon monoxide oxidation is similar to rhodium bismuth on ceria zirconia (Example 6). Therefore, while the inclusion of ceria may be beneficial for other reasons, it is not essential to provide a catalyst having good selectivity.

EXAMPLE 7
Rhodium Bismuth on Alumina

A catalyst containing rhodium and bismuth on alumina is prepared in accordance to the following procedure. 6.7 g of bismuth nitrate pentahydrate is dissolved into 11.1 g of rhodium nitrate solution (9.75% Rh). This precious metal solution is slowly added to 20.0 g gamma alumina and stirred until incipient wetness is achieved which may not require all of the precious metal solution. This impregnated material is then dried at approximately 120° C. As needed, the previous two steps are repeated until all of the precious metal solution has been used. The impregnated material is slurried to approximately 50% solids in water and placed into a jar with a suitable grinding media and milled until a median particle size of approximately 5 microns is achieved. A rotary evaporator removes water from the slurry which is subsequently oven dried at 120° C. 4.0 g of catalyst is slurried to 45% solids with water and coated onto a monolith using the process described above. The sample is then calcined at 850° C. for ten (10) minutes.

Figure 12:
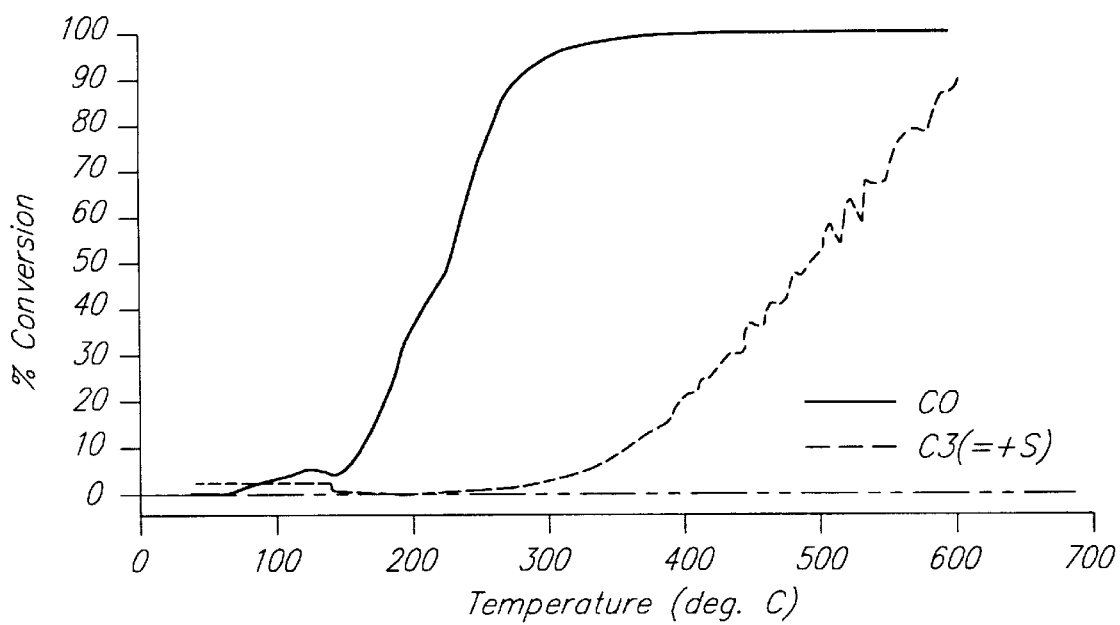
FIG. 12 is an exemplary plot which graphically illustrates the catalytic evaluation of the CO selective combustible catalyst set forth below in example 7 for the percent conversion of carbon monoxide and propane and propylene as a function of temperature.

Catalytic evaluation of this material is shown in FIG. 12. As can be seen from FIG. 12, the selectivity of this catalyst for carbon monoxide oxidation is less effective than rhodium bismuth on ceria zirconia or zirconia. Therefore, the material selection of the support has an influence on selectivity. While not presently preferred, this catalyst composition provides an operable alternative to other compositions disclosed herein.

EXAMPLE 8
Rhodium Bismuth Oxide on Ceria Zirconia

A catalyst containing Rhodium and bismuth oxide on a ceria stabilized zirconia support is prepared in accordance to the following procedure. 40 g of $CeO_2/ZrO_2$ support are impregnated with 10.8 g of aqueous rhodium nitrate solution (10.08% Rh). 4.3 g of zirconium hydroxide paste (27% solids) are added to the impregnated material, slurried to 40%–50% solids and ball milled for forty-five (45) minutes. A rotary evaporator removes water from the slurry which is subsequently oven dried at 120° C. 4.0 g of catalyst is slurried with 0.76 g of bismuth oxide to 45% solid with water in preparation for coating onto a monolith using the process described above.

Figure 13:
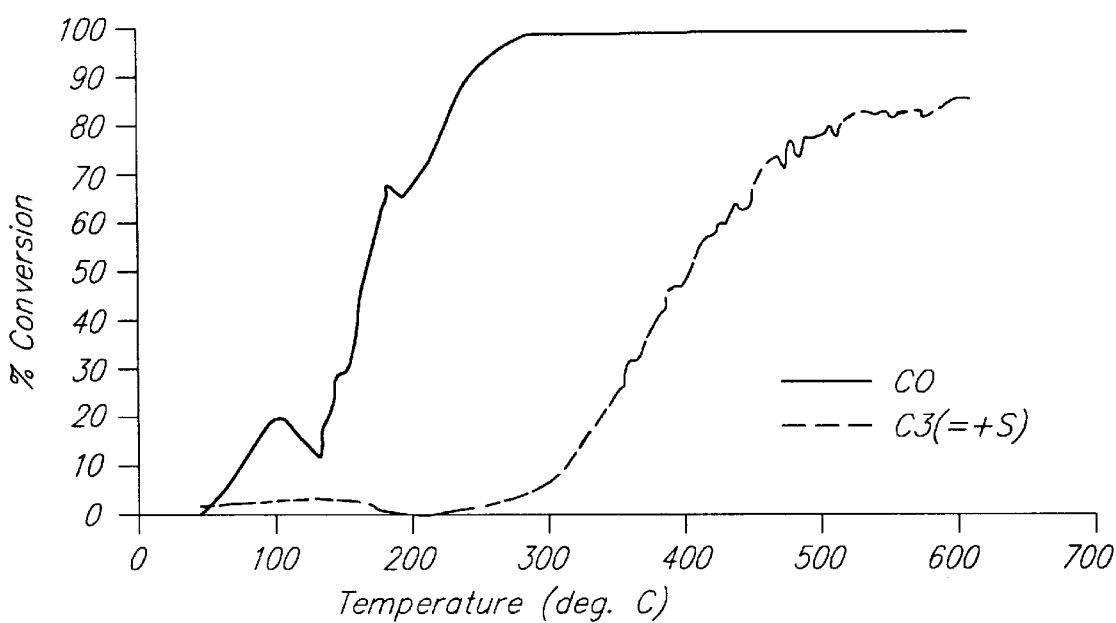
FIG. 13 is an exemplary plot which graphically illustrates the catalytic evaluation of the CO selective combustible catalyst set forth below in example 8 for the percent conversion of carbon monoxide and propane and propylene as a function of temperature.

Catalytic evaluation of this material is shown in FIG. 13. As can be seen from FIG. 13, the selectivity for carbon monoxide oxidation for this catalytic composition is less effective than the selectivity of other catalytic compositions, particularly, Examples 5 and 6, thereby indicating that the rhodium and bismuth must be intimately contacted to optimized selectivity. While not presently preferred, this catalyst composition provides an operable alternative to other compositions disclosed herein.

EXAMPLE 9
Rhodium Bismuth Catalyst from Frit

A catalyst containing Rhodium on a ceria stabilized zirconia support is prepared in accordance to the following procedure using a melting frit having a composition of 81.41% $Bi_2O_3$, 2.91% $Al_2O_3$, 8.76% $B_2O_3$ and 6.92% $SiO_2$. 40.0 g of $CeO_2/ZrO_2$ support are impregnated with 10.8 g of aqueous rhodium nitrate solution (10.08% Rh). 4.3 g of zirconium hydroxide paste (27% solids) are added to the impregnated material, slurried to 40%–50% solids and ball milled for forty-five (45) minutes. A rotary evaporator removes water from the slurry which is subsequently oven dried at 120° C. 4.0 g of catalyst and 0.44 g of frit are slurried to 45% solid with water in preparation for coating onto a monolith using the process described above.

Figure 14A:
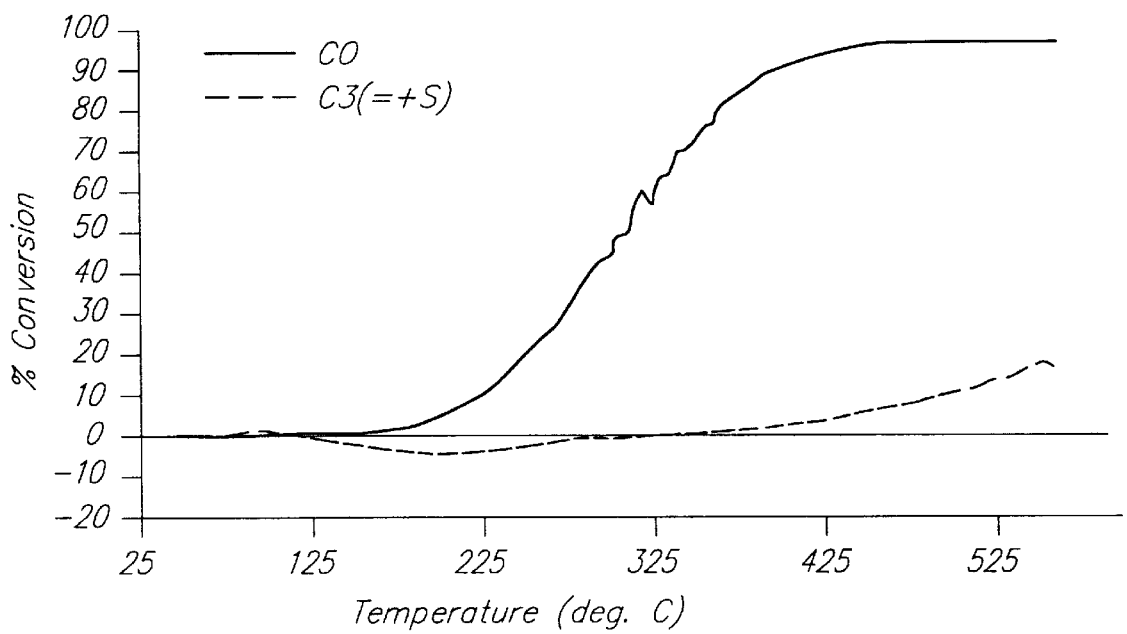
FIG. 14a is an exemplary plot which graphically illustrates the catalytic evaluation of the CO selective combustible catalyst set forth below in example 9 for the percent conversion of carbon monoxide and propane and propylene as a function of temperature.

Catalytic evaluation of this material is shown in FIG. 14*a*. As can be seen from FIG. 14*a*, the carbon monoxide selectivity is similar to Examples 5 and 6.

Figure 14B:
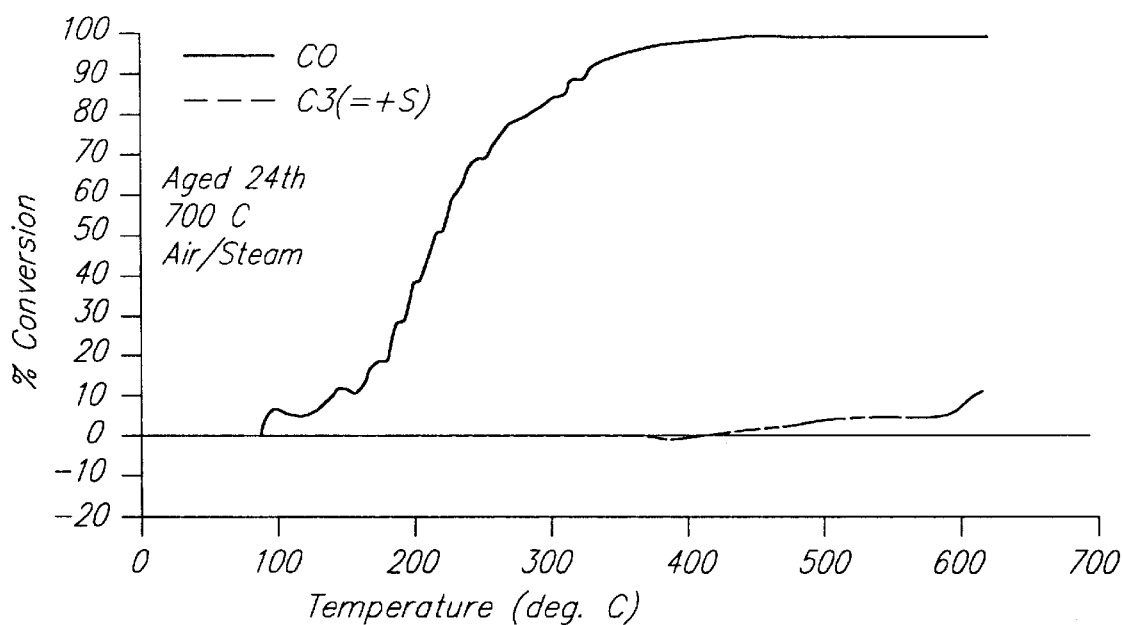
FIG. 14b is an exemplary plot which graphically illustrates the catalytic evaluation of the CO selective combustible catalyst set forth below in modified example 9 for the percent conversion of carbon monoxide and propane and propylene as a function of temperature.

Optionally, the coated monolith can be steamed in 12% steam-88% air at 700° C. for 24 hours. Catalytic evaluation of the steamed catalyst is shown in FIG. 14*b*. A comparison of FIGS. 14*a* and 14*b* indicates the activity and selectivity for carbon monoxide oxidation both improved with steaming.

EXAMPLE 10
Platinum Bismuth on Ceria Zirconia

A catalyst containing platinum and bismuth on a ceria stabilized zirconia support is prepared in accordance to the following procedure using a melting frit having a composition of 81.41% $Bi_2O_3$, 2.91% $Al_2O_3$, 8.76% $B_2O_3$ and 6.92% $SiO_2$. 40.0 g of $CeO_2/ZrO_2$ support are impregnated with a solution containing 7.7 g aqueous platinum amine hydroxide solution (15.54% Pt) and 1.2 ml of acetic acid. 4.3 g of zirconium hydroxide paste (27% solids) are added to the impregnated material, slurried to 40%–50% solids and ball milled for forty-five (45) minutes. A rotary evaporator removes water from the slurry which is subsequently oven dried at 120° C. 4.0 g of catalyst and 0.44 grams of frit are slurried to 45% solid with water in preparation for coating onto a monolith using the process described above.

Figure 15:
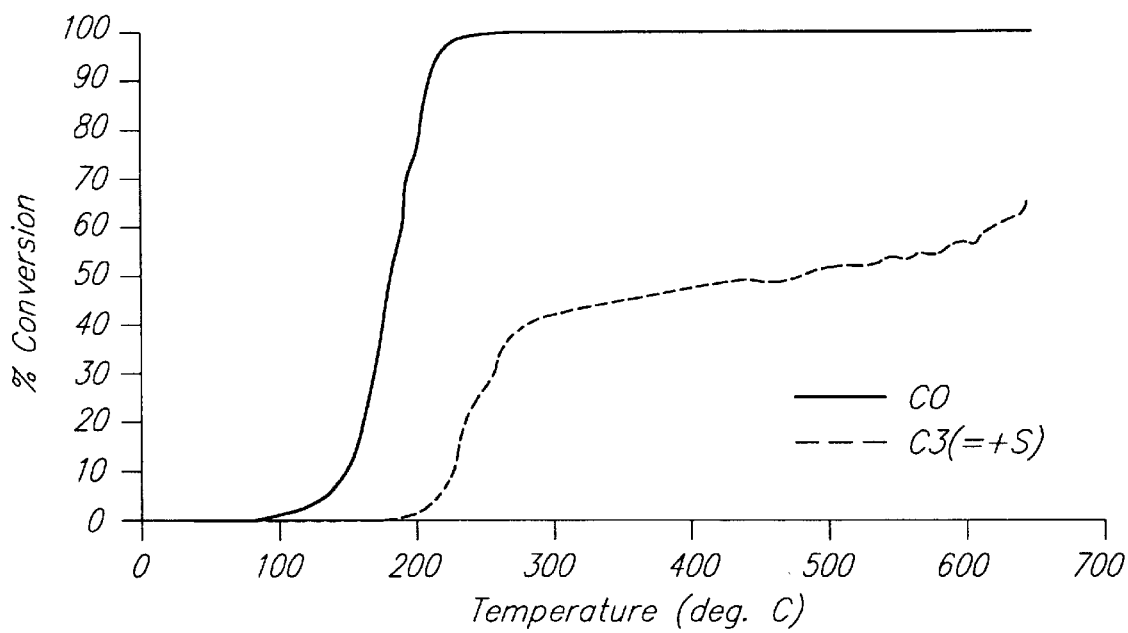
FIG. 15 is an exemplary plot which graphically illustrates the catalytic evaluation of the CO selective combustible catalyst set forth below in example 10 for the percent conversion of carbon monoxide and propane and propylene as a function of temperature.

Catalytic evaluation of this material is shown in FIG. 15. As can be seen in FIG. 15, hydrocarbon oxidation is suppressed somewhat, however the carbon monoxide selectivity is also less effective than the rhodium analog. While not presently preferred, this catalyst composition provides an operable alternative to other compositions disclosed herein.

EXAMPLE 11
Palladium Bismuth on Ceria Zirconia

A catalyst containing palladium and bismuth on a ceria stabilized zirconia support is prepared in accordance to the following procedure using a melting frit having a composition of 81.41% $Bi_2O_3$, 2.91% $Al_2O_3$, 8.76% $B_2O_3$ and 6.92% $SiO_2$. 20.0 g of $CeO_2/ZrO_2$ support are impregnated with 2.5 g palladium nitrate solution (20.84% Pd). 2.2 g of zirconium hydroxide paste (27% solids) are added to the impregnated material, slurried to 40%–50% solids and ball milled for forty-five (45) minutes. A rotary evaporator removes water from the slurry which is subsequently oven dried at 120° C. 4.0 g of catalyst and 0.44 g of frit are slurried to 45% solid with water in preparation for coating using standard coating procedures.

Figure 16:
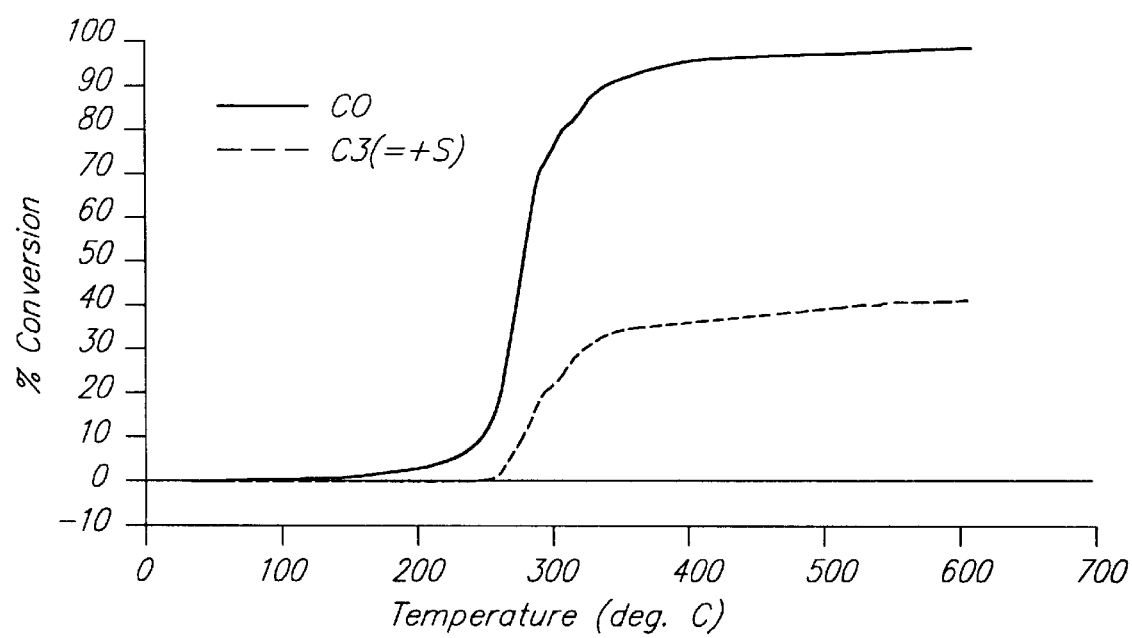
FIG. 16 is an exemplary plot which graphically illustrates the catalytic evaluation of the CO selective combustible catalyst set forth below in example 11 for the percent conversion of carbon monoxide and propane and propylene as a function of temperature.

Catalytic evaluation of this material is shown in FIG. 16. As can be seen from FIG. 16, hydrocarbon oxidation is suppressed somewhat. However, the carbon monoxide selectivity is also less effective than the rhodium analog. While not presently preferred, this catalyst composition provides an operable alternative to other compositions disclosed herein.

Hydrocarbon Gas Sensor Placement

As previously discussed, a primary use for the present invention is to provide a signal corresponding to hydrocarbon concentrations, particularly non-methane hydrocarbon, for the purpose of evaluating the performance of a catalytic converter associated with an automotive vehicle in accordance with on-board diagnostics (OBD) regulations. The differential calorimetric hydrocarbon gas sensor provides a signal that correlates to non-methane hydrocarbon concentrations in exhaust gas under a wide range of operating conditions, e.g., exhaust gas flow rate, exhaust gas temperature, air-to-fuel ratio (AFR) and pre-converter and post-converter locations. While the present invention includes many features intended to render the device significantly independent of these operating conditions, complete independence cannot be achieved, thereby making sensor placement significant. In this regard, appropriate sensor placement is dictated by the exhaust gas flow pattern through the exhaust system, the exhaust gas temperature, the ability to correlate the air-to-fuel ratio to the hydrocarbon sensor signal (i.e. placement of the sensor with respect to the oxygen sensors), the catalyst temperature, and condensation prevention.

With reference now to FIG. 17, automotive vehicle 200 includes internal combustion engine 202 having exhaust system 204 operatively connected thereto. Engine control unit 264 includes control circuitry 300 (FIG. 20) for operating sensor assembly 216. Exhaust system 204 includes drop down pipe 206 connected at a first end to engine 202 at an exhaust manifold (not shown) and connected at a second end to the inlet of catalytic converter 208. Intermediate pipe 210 is connected at a first end to the outlet of catalytic converter 208 and extends toward the rear of vehicle 200 where it is connected with the inlet of muffler 212. Tail pipe 214 has a first end which is connected to the outlet of muffler 212 and a second end which is open to the atmosphere. Exhaust gas sensor assembly 216 of the present invention may be located at any point rearward of catalytic converter 208 in a substantially straight portion of the exhaust system, but may preferably located in a catalytic converter mid-bed location or in close proximity of a light-off converter. For example, exhaust gas sensor assembly 216 could be located in the straight portion 210*a* of intermediate pipe 210 directly aft of catalytic converter 208, in the straight portion 210*b* of intermediate pipe 210 directly forward of muffler 212, or alternately in the straight portion 214a of tail pipe 214 directly aft of muffler 212. Placement of exhaust gas sensor assembly 216 in a substantially straight portion of the exhaust system minimizes the effects of flow turbulence and permits the sensor to be inserted substantially perpendicular into the exhaust gas flow. By providing an orientation substantially perpendicular to the exhaust gas flow results in more reproducible results and minimizes application-to-application variations in sampling and sensor response times, thereby providing accurate evaluation of the catalytic converter.

Figure 18:
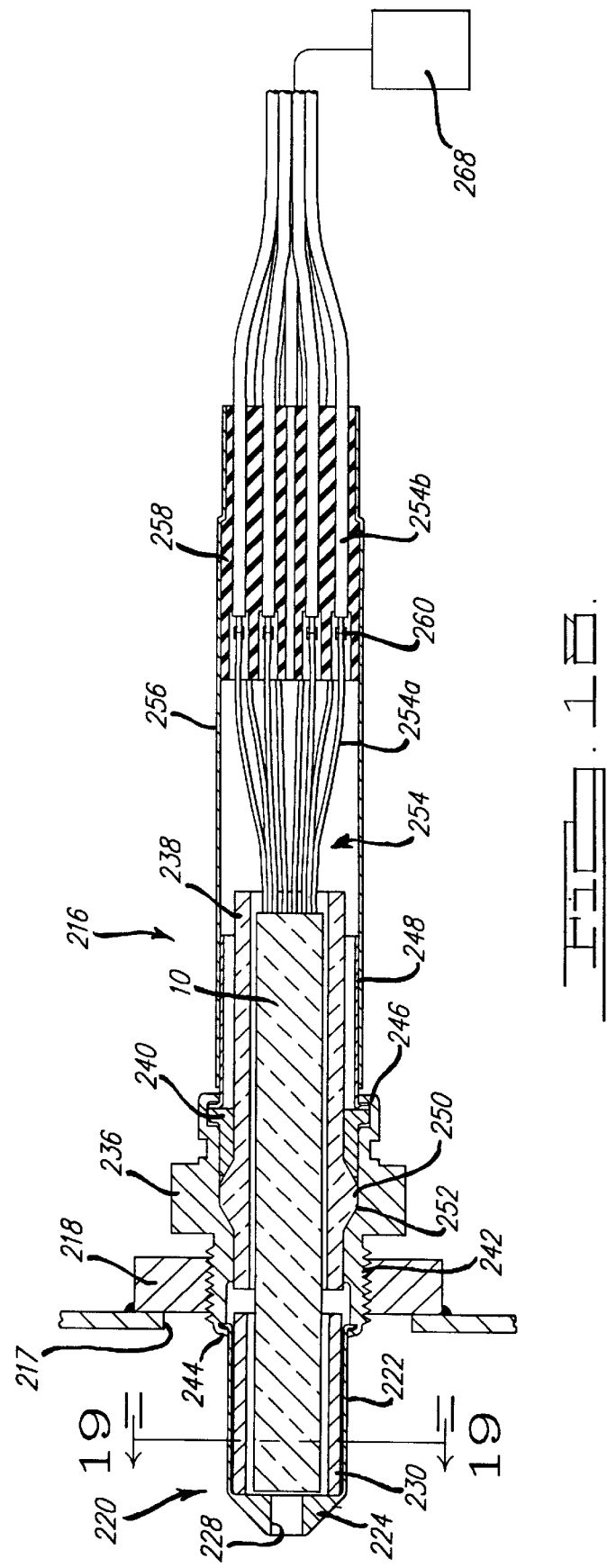
FIG. 18 is a cross-sectional view of the exhaust gas sensor assembly of the present invention.

Sensor element 10 is readily adaptable for use in a variety of housing assemblies for appropriate positioning within exhaust systems 204. Referring now to FIGS. 18 and 19, a presently preferred housing assembly is illustrated. More particularly, exhaust gas sensor assembly 216 is inserted through aperture 217 formed in the side wall of exhaust system 204 and held in position by nut 218 which is welded to an exterior surface of exhaust system 204. An end of sensor assembly 216 extends inwardly into exhaust system 204 and into the exhaust gas flow occurring therein. Sensor assembly 216 includes an outer shroud 220 having a cylindrical side wall 222 and a frustoconical cap 224 formed thereon. A plurality of inlet ports 226 are formed through cylindrical side wall 222 for providing communication from exhaust system 204 into sensor assembly 216. Similarly, outlet port 228 is formed through cap portion 224 and provides fluid communication from sensor assembly 216 to exhaust system 204. Inner shroud 230 is operatively disposed within outer shroud 220 to define a plurality of channels 232 directly adjacent inlet port 226. More specifically, the outer surface of inner shroud 230 has a plurality of longitudinally extending flutes 233 formed therein to provide a fluid flow path from exhaust system 204 through inlet port 226 down channel 232 into inner cavity 234 formed in inner shroud 230. Portions of cylindrical side wall 222a, 222b are deformed radially inwardly into flute 233 to provide means for mechanically locating inner shroud 230 with respect to outer shroud 220.

Sensor element 10 is disposed within and substantially divides interior cavity 234 into interior catalyst cavity 234a and interior oxygen source cavity 234b. Presently, sensing element 10 is positioned adjacent to but not in direct contact with inner shroud 230. However, in certain circumstances it may be desirable to secure sensing element 10 directly to the interior of inner shroud 230. As presently preferred, outer shroud 220 and inner shroud 230 are manufactured from 303 stainless steel or an engineering approved equivalent thereof. However, one skilled in the art would readily recognize that inner shroud 230 could also be manufactured from a ceramic-type composite material.

With continued reference to FIG. 18, sensor assembly 216 further includes threaded fitting 236, ceramic insert 238 and ferrule 240 for adequately supporting sensing element 10 therein. Threaded fitting 236 includes a threaded portion 242 which engages nut 218 to secure sensor assembly 216 to exhaust system 204. Roll flange 244 is formed on an end of threaded fitting 236 for capturing a complementary flange formed on cylindrical side wall 222 of outer shroud 220. Similarly, roll flange 246 is formed on an opposite end of threaded fitting 236 for capturing a complementary flange formed on roll sleeve 248. Ceramic insert 238 is received within threaded fitting 236 to circumscribe and appropriately position sensing element 10 in sensor assembly 216. More particularly, ceramic insert 238 is substantially cylindrical and has a ring portion 250 formed on an outer surface thereof which engages a shoulder portion 252 formed in threaded fitting 236. Ferrule 240 is received within threaded fitting 236 to circumscribe ceramic insert 238 and engage ring 250 opposite shoulder 252. Roll flange 246 captures and secures ferrule 240, thereby providing a compression-type fitting therein. Electrical leads 254 provide an electrical connection between sensor 10 and external electronic control device 268. Crimp tube 256 and plug bushing 258 extend from roll sleeve 248 for preventing electrical leads 254 from becoming disconnected from sensor element 10. More specifically, crimp tube 256 slides over and engages an outer wall of roll sleeve 248. Plug bushing 258 is disposed within an end of crimp tube 256 and compliantly secures electrical leads 254 therein. Optionally, butt crimp connectors 260 are utilized to connect sensor leads 254a with control device leads 254b and further provide physical restraint against axial loading of these leads. As presently preferred, roll sleeve 248 and crimp tube 256 are fabricated from 303 stainless steel or an engineering approved equivalent thereof. Plug bushing 258 is fabricated from an appropriate high temperature insulating material such as a silicone based rubber or an engineering approved equivalent thereof.

Sensor assembly 216 protrudes into a pipe of exhaust system 204 such that outer shroud 220 and inner shroud 230 cover sensor element 10. Ports 226 and channels 232 therein are engineered to direct exhaust gas along a tortuous path down along a longitudinal axis of sensor assembly 216 and back into inner cavity 234 past sensing element 10. Gas flow past the sensor element 10, the placement of the sensor assembly 216 and particularly the shape of cap 224 ad port 228 create a pressure differential between inner cavity 234 and the exhaust gas flow. While exhaust gas flow through the sensor is dependent upon the exhaust gas flow and the housing design, sensor assembly 216, and more particularly the tortuous path defined therein, creates a substantially laminar flow of exhaust gas past the sensing element, thereby minimizing exhaust gas flow turbulence.

Appropriate placement of sensor assembly 216 is also dictated by the exhaust gas temperature surrounding sensor assembly 216. The present invention preferably operates at a temperature below approximately 600° C. However, in order to operate, the exhaust gas temperature must be lower than the sensor temperature. Operation at higher temperature may lead to premature aging and poisoning of the catalyst materials, for example $SO_2$ of the catalyst. When the vehicle is operated using fuels with sulfur content exceeding 50 parts-per-million (ppm) it is preferred to operate at lower temperatures. Where lower sulfur content fuels are available, such as reformulated fuels with sulfur content less than 20 ppm, operation is preferably at temperatures of about 400° C.–550° C. to obtain optimum selectivity of the catalysts, but may be in the range of 300° C.–700° C. Accordingly, placement of the sensor 216 in a location that will, under normal vehicle operating conditions, not allow the sensing element to exceed 600° C. is desirable. Placement of sensor assembly 216 substantially downstream of catalytic converter 208, such as at location 210b, will typically ensure that exhaust gas passing through sensor assembly 216 will not exceed 750–850° C. and may reduce the risk of catalyst poisoning since the catalytic converter 216 will scavenge potentially poisoning substances. In any event, exact placement of sensor assembly 216 will depend on the vehicle, engine size, and exhaust piping configuration.

As previously indicated, sensor assembly 216 will provide a signal which correlates to exhaust gas non-methane hydrocarbon concentrations. The conversion efficiency of catalytic converter 208 at sufficiently high temperatures (greater than 600° C.) becomes mass transfer limited and therefore essentially temperature independent. However, at temperatures closer to light off (300–500° C.), the conversion efficiency of catalytic converter 208 is related to catalyst temperature and exhaust gas temperatures. To better utilize the sensor signal for catalyst diagnosis it is desirable to know the temperatures of catalytic converter 208 and the exhaust gas corresponding to a given sensor signal in order to correlate the sensor signals with converter performance.

As previously discussed, sensor assembly 216 is provided with electrochemical oxygen source 18 to ensure complete oxidation of the combustibles within the exhaust gas reaching sensing element 10. When operating in this manner, sensor assembly 216 will be substantially independent of the air-to-fuel ratio (AFR) and provide a signal which directly correlates to non-methane hydrocarbon concentrations in the exhaust gas flow. However, in some applications it is desirable to provide a relationship between the hydrocarbon sensor signal output and the exhaust gas air-to-fuel ratio signal. To best correlate the hydrocarbon sensor output signal with the exhaust gas air-to-fuel ratio signal, it is desirable to place sensor assembly 216 in close proximity to an air-to-fuel ratio sensor 262. If these sensors cannot be placed in close proximity, it is desirable to determine the separation volume, i.e., the volume between the hydrocarbon sensor and the AFR sensor, as well as the exhaust gas flow rate and the response times for these sensors, such that the sensor signals for these sensors can be correlated for converter monitoring purposes.

Sensor assembly 216 will experience condensation build-up owing to the exceptionally high levels of water in the exhaust gas flow during cool down after engine shutoff. Extensive condensation build-up within sensor assembly 216 may damage sensing element 10 in several ways, including element cracking or housing bending, delamination of diffusion barrier 32 from substrate 26 or destruction of electrochemical oxygen source 18. Accordingly, to prevent build-up of condensation, sensor assembly 216 should be placed within exhaust system 204 such that inlet port 226 and outlet port 228 are pointed at least slightly downwardly to enable drainage of any condensate. Preferably sensor assembly 216 is vertically oriented directly down into exhaust system 204. However, limited clearances under a floor pan of automotive vehicle 202 may render this orientation impractical. Thus, sensor assembly 216 should be oriented at least slightly downwardly to permit drainage of condensate therefrom. In addition to appropriate positioning of sensor assembly 216 for water drain-off, start-up procedures for sensor assembly 216 may incorporate either an exhaust gas flow soak period, i.e., exposure to exhaust gas prior to activation of sensor 216, in which sensor element 10 is warmed by exhaust gas flow, or a feedback controlled heat-up by compensation heaters 50a, 50b and primary heaters 58, 62, either process having the effect of warming up sensor element 10 thereby abating any water and/or ice within sensor assembly 216.

Operation of Hydrocarbon Gas Sensor

In general, the sensor of the present invention operates to maintain temperature sensitive elements 46a and 46b at a substantially constant temperature in view of the chemical heat released and the electrical power dissipated. With continued reference to FIGS. 1–3 and FIG. 20, the operation of the present invention is described. Voltage is applied to primary heaters 58 and 62 and compensation heaters 50a, 50b to bring differential calorimetric hydrocarbon gas sensor 10 to a predetermined stable temperature as measured by temperature-sensitive element 46b, preferably approximately 600° C. As exothermic oxidation reactions occur on active surfaces 34a, 34b, different temperature rises of catalytic surface 34a and reference surface 34b resulting from the heat released by the oxidation reactions are detected by temperature-sensitive elements 46a, 46b. Control circuitry 300 compensates for the difference in the temperature rise detected at temperature-sensitive elements 46a, 46b by adjusting the applied voltage or current flowing in compensation heater 50a to adjust the electrical power dissipated in compensation heater 50a until the temperature of temperature-sensitive elements 46a, 46b is equal. Accordingly, the power adjustment to compensation heater 50a that is necessary to balance temperature-sensitive elements 46a, 46b is proportional to the difference in the exothermic oxidation heat generated by the catalytic reactions.

In practice, the power supplied to compensation heaters 50a, 50b is controlled by control circuitry 300 and the voltage across each compensation heater 50a, 50b is measured by control circuitry 300. Voltage measurement is performed by a high impedance device, which does not draw appreciable current. Use of the high impedance device permits the width of the metal traces connected to compensation heaters 50a, 50b, and used to measure the voltage applied to the compensation heaters to be very narrow without inducing unacceptable voltage drops in the heater voltage measurements. The metal traces carrying current to compensation heaters 50a, 50b have sufficient width to ensure that the heat dissipated in the traces is limited, and does not degrade the power difference measurement used to determine the difference in the exothermic oxidation heat generated by the catalytic reactions. Moreover, the response time of control circuitry 300 is significantly less than the rate of change of temperature resulting from the oxidation reaction in active region 14a and reference region 14b.

In accordance with the invention, primary heaters 58, 62 and compensation heaters 50a, 50b are arranged within substrate 26 and are used to fix the temperature of substrate 26 as sensed by temperature-sensitive elements 46a and 46b. The arrangement provides a fixed relationship between the power dissipated in the compensation heaters 50a and 50b and the heat generated by exothermic oxidation reactions occurring at catalysts 34a and 34b. Compensation of the heat generated by oxidation reactions occurring at catalyst 34a and 34b using compensation heaters 50a and 50b reduces the thermal dissipation in intermediate layers 48, 52, 56, 60 and bottom layer 64. The precise thermal management obtained within substrate 26 provides for a rapid response to temperature changes occurring at top layer 44. Accordingly, heat conduction within substrate 26 that would otherwise introduce error in the measurement of heat generated by exothermic oxidation reactions is minimized. Thus, in accordance with the invention, the temperature of top layer 44 varies in proportion to heat generated from oxidation reactions and the thermal response time is determined primarily by the time required for heat to diffuse through top layer 44 to temperature-sensitive elements 46a, 46b. By controlling the temperature variation of all portions of substrate 26 the difference in the power dissipated in the compensation heaters 50a and 50b is proportional to the difference in the heat generated by exothermic oxidation reactions occurring at catalysts 34a and 34b.

Figure 20A:
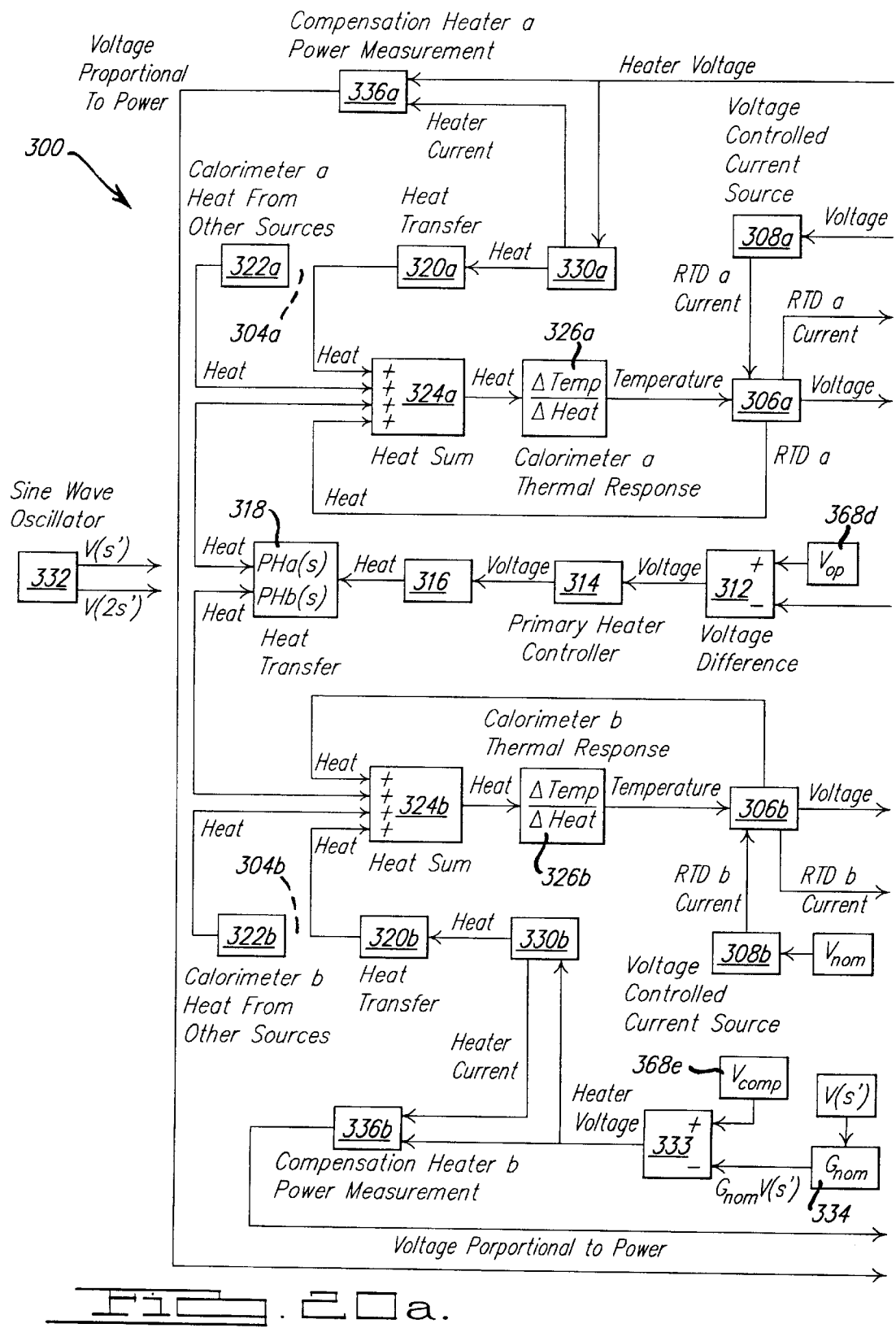
FIG. 20 is a schematic representation of the control scheme of the present invention.
Figure 20B:
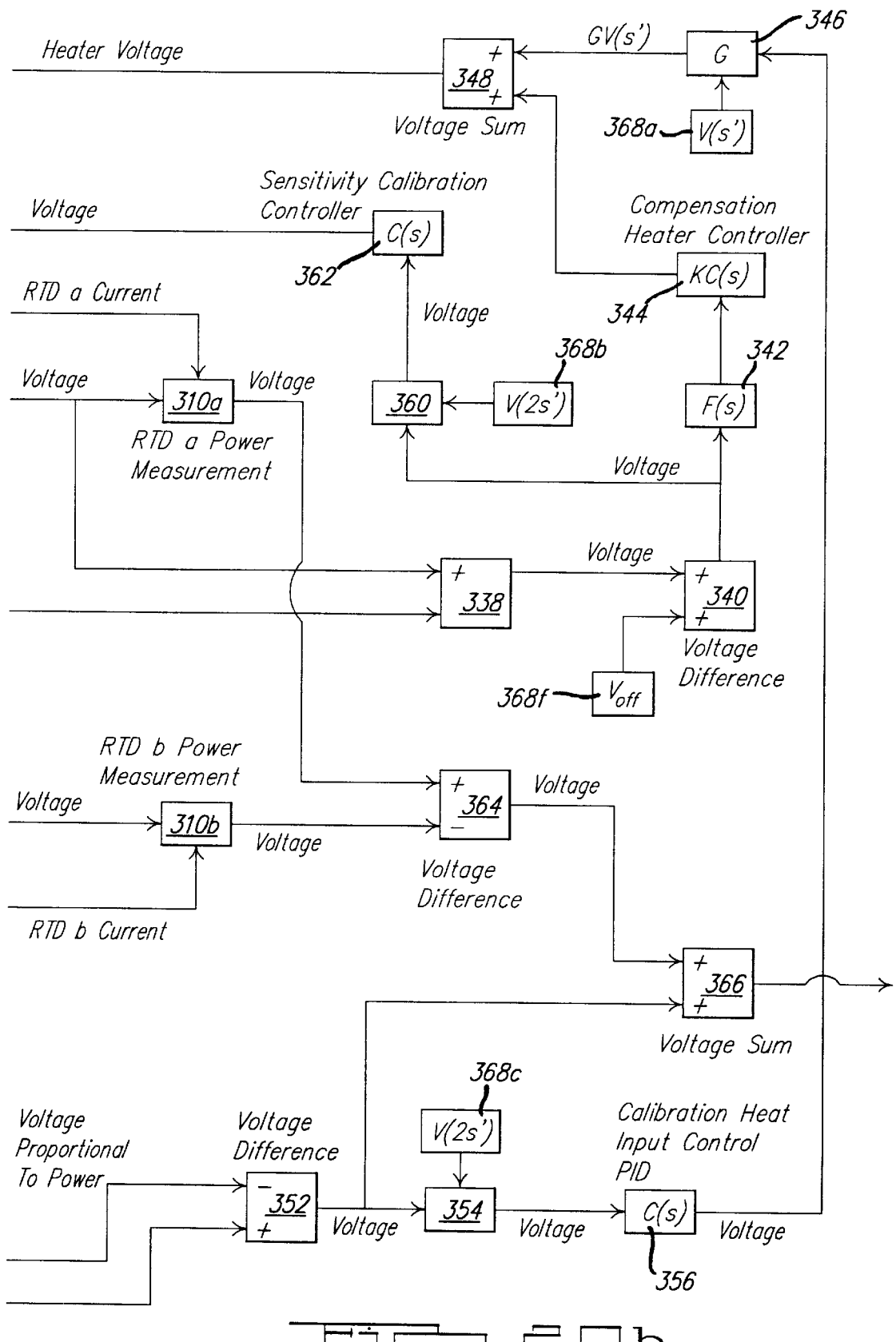

Control circuitry 300 is more fully detailed and its method of operation is described in the aforementioned United States Patent Application entitled "Calorimetric Hydrocarbon Gas Sensor." With reference to FIG. 20, a summary of control circuitry 300 and its operation is provided to enhance understanding of the present invention. As seen in FIG. 20, control circuitry 300 can be grouped according to the functions performed by related circuit elements. A reference power equalization control circuit establishes equal quantities of sinusoidally varying power at frequency 2s' in the compensation heaters. A response equalization circuit establishes equal signals from the temperature-sensitive elements at frequency 2s', in response to the equal quantities of sinusoidally varying power at frequency 2s' in the compensation heaters. A primary heater control circuit maintains reference temperature-sensitive element 46b (shown as 306b in FIG. 20) at constant temperature. A compensation heater control circuit maintains a constant temperature difference between temperature-sensitive elements 46a and 46b (306a and 306b in FIG. 20, respectively). A power difference measurement circuit measures the difference in heat dissipated in the compensation heaters. This difference is proportional to the heat released by catalyzed oxidation in regions 14a and 14b. The output of the power difference measurement circuit is the main output of sensor 10.

The reference power equalization control circuit includes, compensation heaters 330a, 330b, heater power measurement circuits 336a, 336b, voltage comparator 352, demodulator 354, voltage oscillators 368a, 368c, calibration controller 356 and gain circuit 346. The response equalization circuit includes temperature-sensitive elements 306a, 306b, current sources 308a, 308b, voltage difference circuit 338, demodulator 360, voltage oscillator 368b and calibration controller 362. The primary heater control circuit includes primary heater 316 and primary heater controller 314. The compensation heater control circuit includes compensation heaters 330a, 330b, temperature-sensitive elements 306a, 306b, voltage difference circuit 338, voltage sources 368e, 368f, low pass filter 342 and controller 344. The power difference measurement circuit includes power measurement circuits 310a, 310b, 336a, 336b, and voltage comparators 364, 366 and 352.

In an alternative embodiment of the control and measurement circuitry, the resistance of compensation heaters 330a, 330b can be used to provide the required temperature measurement, eliminating the need for temperature-sensitive elements 306a, 306b. The resistance temperature measurement is performed by measuring the ratio of the voltage applied to the heater divided by the current flowing in the heater. Similar to the technique described above, the voltages applied to each heater are adjusted to provide a difference in the power dissipated in each heater that will maintain the two heaters at a substantially constant temperature difference. However, the relative thermal response depends on the values of the currents flowing in the two heaters. Since currents vary as the heater voltages are adjusted to maintain the required difference in power dissipation, they cannot be independently adjusted to equalize the thermal response. Therefore, it is necessary to make response equalization adjustments in the control and measurement circuitry. In addition, the sinusoidally varying powers used in the response equalization process cannot be both produced and measured by the compensation heaters. The sinusoidally varying powers used in the response equalization process could be produced in the primary heaters. In this alternative embodiment, the sensing element is simplified by eliminating the temperature sensing devices, but more elaborate control and measurement circuitry is required.

Simultaneous Combustible Gas and Oxygen Measurement in an Exhaust Gas Stream

Figure 21:
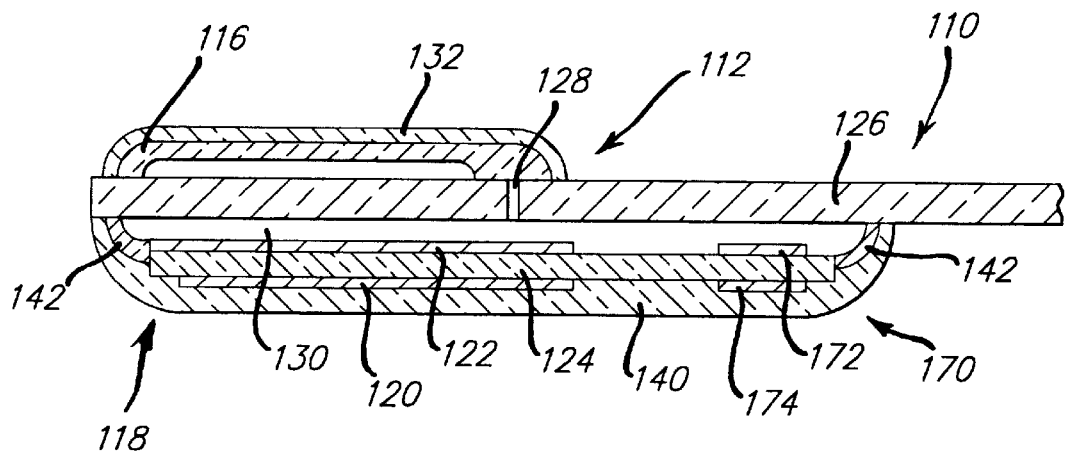
FIG. 21 illustrates modifications to the embodiment of the sensor shown in FIGS. 4–5 for enabling simultaneous measurement of non-methane hydrocarbons and oxygen in the exhaust gas flow.

As previously discussed, in some applications sensor element 10 requires oxygen to be present in order to permit combustion of exhaust gases at catalyst 14. Accordingly, as presently preferred electrochemical oxygen source 18 is incorporated into sensor element 10 decomposes water ($H_2O$) and/or carbon dioxide ($CO_2$) into its constituents, thereby releasing oxygen for use by the sensor. The present invention further contemplates modifications to sensor element 10 in which simultaneous determination of the concentration of oxygen as well as non-methane hydrocarbons in the exhaust gas may be made. FIG. 21 represents a modification to sensor 110 illustrated in FIGS. 4 and 5 which provides for an integral oxygen sensor with sensor 110. Accordingly, like components will be referred to with like reference numerals.

With reference to FIG. 21, an additional pair of electrodes can be added to electrochemical oxygen source 18 such that the combined system is capable of functioning as an oxygen sensor simultaneously with its functioning as a differential calorimetric hydrocarbon gas sensor. More particularly, oxygen exhaust sensor cell 170 is disposed adjacent to electrochemical oxygen source 118 on zirconia electrolyte layer 124. Oxygen sensor cell 170 includes a reference electrode 124 disposed on an inner surface of electrolyte layer 124 within lateral transport layer 130 for providing an oxygen reference signal. A sensing gas 174 is disposed on an outer surface of electrolyte layer 124 and provides an exhaust gas signal. As presently preferred reference electrode 172 and exhaust gas electrode 174 are formed of a noble metal, such as platinum or palladium, which is sufficiently catalytic to reach thermodynamic equilibrium at the surface of oxygen sensor cell 170.

When electrochemical oxygen source 118 is supplying oxygen to sensing element 10, the reaction at exhaust gas electrode 174 is as follows:

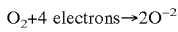

$$O_2 + 4\ electrons \rightarrow 2O^{-2}$$

Under rich conditions, and for stoichiometries just slightly to the lean side, there is insufficient oxygen available to sustain the oxygen reduction reaction set forth above such that the current through oxygen source 118 is sustained by the following two processes:

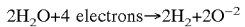

$$2H_2O + 4\ electrons \rightarrow 2H_2 + 2O^{-2}$$

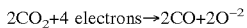

$$2CO_2 + 4\ electrons \rightarrow 2CO + 2O^{-2}$$

In the solid electrolyte layer 124, oxygen ions formed on the cathode side 120 is balanced with the oxygen discharged on the anode side 122. Thus, the following oxygen reduction reaction occurs at cathode electrode 120:

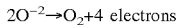

$$2O^{-2} \rightarrow O_2 + 4\ electrons$$

Accordingly, by providing an additional pair of electrodes 172, 174 to the oxygen cell 118 as illustrated in FIG. 21, oxygen sensor cell 170 is formed and can be utilized to sense the external oxygen concentration in the exhaust gas flow.

Oxygen sensor cell 170 can be used in a potentiometric mode and will provide a signal response similar to a lambda sensor (HEGO) now widely used for automotive engine control in providing a sensor element which includes an internal oxygen reference in the form of lateral transport layer 130, thereby eliminating any gas phase connection to the exterior of the sensor element.

Oxygen sensor electrodes 172, 174 may also be operated as a driven cell, in combination with a diffusion barrier and suitable support electronics, to function as a wide range oxygen sensor (UEGO).

Figure 22:
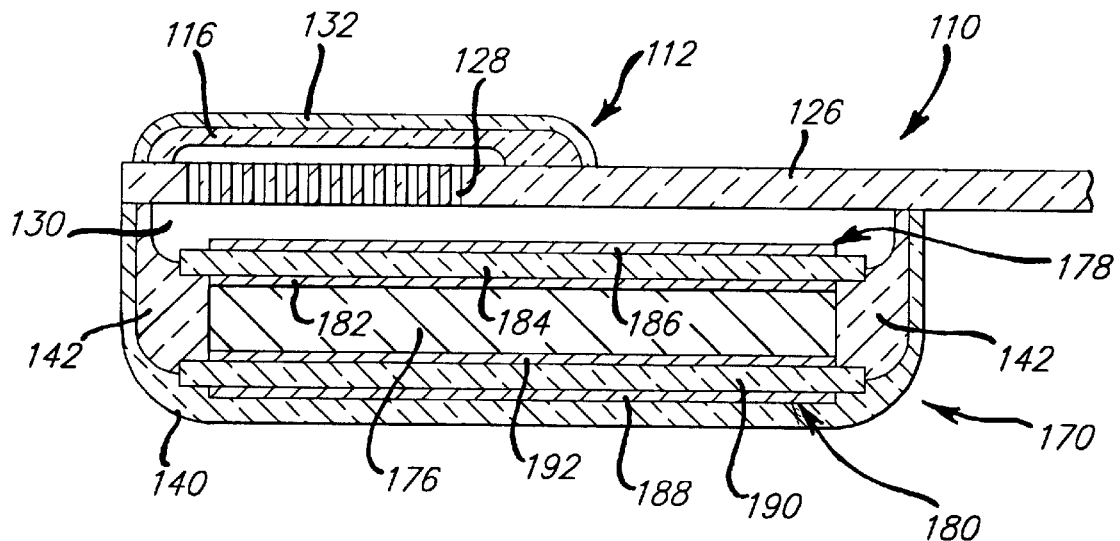
FIG. 22 illustrates modifications of the embodiment of the sensor shown in FIGS. 4–5 and showing in cross-section an alternate preferred embodiment of an oxygen source for use with the present invention.

FIG. 22 illustrates still further modifications to the sensor shown in FIGS. 4–5. Again, like components will be referred to by like reference numerals. As will be described with reference to FIG. 22, the oxygen required to sustain the oxidation reactions set forth above can be supplied by the dissociation of $Fe_2O_3$ to produce $Fe_3O_4$. In a preferred embodiment, the iron oxides in the form of metal oxide layer 176 are situated between oxygen source 178 adjacent to an inner surface of layer 176 and oxygen sensor 180 adjacent an outer surface of metal oxide layer 176. It should be understood that other suitable metal oxides capable of a $M_xO$ to $M_yO$ reaction may be employed without departing from the fair scope of the present invention for providing a source of oxygen. The oxygen available in metal oxide layer 176 may be withdrawn by placing a potential across oxygen source 178. In this manner, oxygen ions are drawn from metal oxide layer 176, through porous platinum electrode 182, yttrium stabilized zirconia electrolyte 184 to porous platinum electrode 186 and hence to oxygen storage region 130.

It is important to recognize that metal oxide layer 176 has a limited supply of oxygen that would be depleted well before the designed service life of sensor 110. It is possible to operate the oxygen source in reverse, thereby drawing oxygen from oxygen storage region 130 to metal oxide layer 176, to replenish the oxygen in metal oxide layer 176. In a preferred embodiment, oxygen sensor 180 including porous platinum electrodes 188, 192 and yttrium stabilized zirconia electrolyte 190 is operated in an amperometric mode to advantageously provide a source of oxygen for replenishing the oxygen within metal oxide layer 176. Oxygen sensor 180 operates by drawing oxygen from the free exhaust gas stream through porous protective layer 140, to metal oxide layer 176. The oxygen flux, or current conducted at a given voltage is proportional to the amount of free oxygen present in the exhaust gas. Hence, an oxygen measuring device as well as a means for replenishing the oxygen in metal oxide layer 176 is provided. It should also be recognized that oxygen sensor 180 may also be operated in a potentiometric mode.

Use of metal oxide layer 176 offers the further advantage of allowing the yttrium stabilized zirconia electrolyte layers 182, 184 sandwiched between porous platinum electrodes 186, 188 and 190, 192, respectively, to be made exceedingly thin. It is known that the efficiency of oxygen source 178 and oxygen sensor 180 are enhanced through the use of thinner yttrium stabilized zirconia electrolyte layers. However, because yttrium stabilized zirconia is very brittle, it does not lend itself to being made very thin and in such configurations would be unsuitable for use in sensor 110. Metal oxide layer 176 placed in contact with the oxygen source 178 and oxygen sensor 180 offers structural support for the yttrium stabilized zirconia layers 184, 190, respectively, thus allowing for thinner construction.

Metal oxide layer 176 offers the additional advantage of providing an oxygen partial pressure reference. It should be noted that the reference values will vary with temperature. However, metal oxide layer is situated in good thermal contact with substrate 126 which is maintained at constant temperature during sensor operation thereby holding the reference constant. The stable partial pressure reference enables placing oxygen sensor 180 on the outer surface of metal oxide layer 176 for operation as either a wide range oxygen sensor in an amperometric mode or as a potentiometric mode oxygen sensor.

From the detailed description set forth above, it is apparent that there has been provided, in accordance with the invention, a differential calorimetric hydrocarbon gas sensor that fully meets the advantages set forth above. Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications as fall within the scope of the appended claims and equivalents thereof.

We claim:

1. A differential calorimetric hydrocarbon gas sensor for determining the concentration of hydrocarbon gas species in a gas flow comprising:

a sensing element located within a sensing region and including a catalytic layer having a first catalyst and a second catalyst disposed on the catalytic layer, the first catalyst having an active region comprising a total combustible catalyst having an active metal component selected form the group consisting of: platinum, rhodium, palladium, iridium, ruthenium, and combinations thereof, and the second catalyst differing from the first catalyst in its catalytic activity for oxidation of hydrocarbons;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry;

a diffusion barrier overlying the catalytic layer for controlling the rate at which the gas diffuses to the catalytic layer and for protecting the catalytic layer from scouring by the gas flow;

a transport layer interposed between the diffusion barrier and the catalytic layer for further controlling the rate at which the gas flow diffuses to the catalytic layer;

an oxygen source, the oxygen source and the sensing region being disposed on a region of the sensor that is commonly heated; and whereby the concentration of hydrocarbon species in a gas flow can be determined from the sufficient quantity of heat generated by the temperature compensation circuitry and measured by the temperature reference circuitry.

2. The differential calorimetric sensor of claim 1 wherein the first catalyst active region accelerates the oxidization of substantially all residual combustible gases present in the gas flow, and the second catalyst has a reference region which selectively accelerates the oxidization of carbon monoxide and hydrogen present in the gas flow.

3. The differential calorimetric sensor of claim 1 wherein the active region comprises a total combustible catalyst having an active metal component selected from the group consisting of: platinum, rhodium, palladium and combinations thereof.

4. The differential calorimetric sensor of claim 1 wherein the active region comprises a total combustible catalyst having an active metal component including a combination of platinum and rhodium.

5. The differential calorimetric sensor of claim 1 wherein the active region comprises a total combustible catalyst having an active metal component supported on a stable refractory support selected from the group consisting of: alumina, zirconia, titania, silica, silica alumina and combinations thereof.

6. The differential calorimetric sensor of claim 5 wherein the refractory support includes an oxygen storage material.

7. The differential calorimetric sensor of claim 6 wherein the oxygen storage material includes ceria.

8. The differential calorimetric sensor of claim 1 wherein the active region comprises a total combustible catalyst having an active metal component supported on a high surface area, stable refractory support including gamma alumina.

9. The differential calorimetric sensor of claim 8 wherein the refractory support includes an oxygen storage material.

10. The differential calorimetric sensor of claim 9 wherein the oxygen storage material includes ceria.

11. The differential calorimetric sensor of claim 1 wherein the active region comprises a total combustible catalyst having an active metal component supported on a refractory support including a combination of precalcined alumina and ceria stabilized zirconia.

12. The differential calorimetric sensor of claim 1 wherein the active region comprises a total combustible catalyst selected from the group consisting of: platinum and rhodium on prestabilized alumina, platinum and rhodium on ceria alumina, and rhodium on ceria stabilized zirconia.

13. The differential calorimetric sensor of claim 1 wherein the reference region comprises a selective combustible catalyst having an active metal component selected from the group consisting of: rhodium, bismuth, palladium, platinum and combinations thereof.

14. The differential calorimetric sensor of claim 1 wherein the reference region comprises a selective combustible catalyst having an active metal component selected from the group consisting of: rhodium, bismuth and combinations thereof.

15. The differential calorimetric sensor of claim 1 wherein the reference region comprises a selective combustible catalyst having an active metal component including a combination of rhodium and bismuth.

16. The differential calorimetric sensor of claim 15 wherein the active metal component comprises a combination of rhodium and bismuth having an atomic ratio in the range of 0.5–3.0.

17. The differential calorimetric sensor of claim 16 wherein the active metal component comprises a combination of rhodium and bismuth having an atomic ratio in the range of 1.0–2.5.

18. The differential calorimetric sensor of claim 15 wherein the rhodium and bismuth are combined as a solution of soluble salts.

19. The differential calorimetric sensor of claim 1 wherein the reference region comprises a selective combustible catalyst having an active metal component supported on a stable refractory support selected from the group consisting of: alumina, zirconia, and combinations thereof.

20. The differential calorimetric sensor of claim 19 wherein the refractory support includes an oxygen storage material.

21. The differential calorimetric sensor of claim 20 wherein the oxygen storage material includes ceria.

22. The differential calorimetric sensor of claim 20 wherein the refractory support includes ceria stabilized zirconia.

23. The differential calorimetric sensor of claim 1 wherein the reference region comprises a CO selective catalyst selected from the group consisting of: rhodium and bismuth on ceria zirconia, rhodium and bismuth on zirconia, rhodium and bismuth on alumina, rhodium and bismuth on ceria zirconia, rhodium and bismuth from frit, platinum and bismuth on ceria zirconia, and palladium and bismuth on ceria zirconia.

24. The differential calorimetric sensor of claim 1 wherein the sensing region is supported on a substrate and the oxygen source comprises an electrochemical oxygen source.

25. The differential calorimetric sensor of claim 24 wherein the electrochemical oxygen source further comprises:
    an first electrode disposed in spaced relation to the substrate such that an oxygen storage region is formed therebetween;
    an electrolytic layer disposed adjacent the first electrode opposite the oxygen storage region;
    a second electrode disposed adjacent to the electrolytic layer; and
    at least one via formed in the substrate in communication with the oxygen storage region.

26. The differential calorimetric sensor of claim 25 wherein the first and second electrodes are porous platinum electrodes and the electrolytic layer is yttrium stabilized zirconia.

27. The differential calorimetric sensor of claim 24 further comprising a porous protective layer overlying the oxygen source.

28. The differential calorimetric sensor of claim 1 further comprising a substrate including:
    a first layer having the catalytic layer disposed thereon;
    a second layer positioned adjacent to the first layer and having the temperature reference circuitry disposed thereon;
    a third layer positioned adjacent to the second layer and having the temperature compensation circuitry disposed thereon;
    an oxygen source positioned adjacent to the third layer; and
    the first, second and third layers having at least one via formed therethrough to provide fluid communication between the oxygen source and the sensing region.

29. The differential calorimetric sensor of claim 28 wherein the temperature reference circuitry further comprises:
    a first temperature-sensitive element disposed on the second layer below the first catalyst for measuring the temperature of the first catalyst; and
    a second temperature-sensitive element disposed on the second layer below the second catalyst for measuring the temperature of the second catalyst.

30. The differential calorimetric sensor of claim 29 wherein the first temperature-sensitive element and the second temperature-sensitive element are resistive temperature devices.

31. The differential calorimetric sensor of claim 29 wherein the temperature compensation circuitry further comprises:
    a first heat-generating element disposed on the third layer below the first catalyst for maintaining the first catalyst at the first substantially constant operating temperature; and
    a second heat-generating element disposed on the third layer below the second catalyst for maintaining the second catalyst at the second substantially constant operating temperature.

32. The differential calorimetric sensor of claim 31 wherein the first heat-generating element and the second heat-generating element are resistance-based heating elements.

33. The differential calorimetric sensor of claim 29 further comprising:
   a fourth layer positioned adjacent to the third layer;
   a fifth layer positioned adjacent to the fourth layer;
   the fourth and fifth layers having at least one via formed therethrough and aligned with the at least one via of the first, second and third layers to provide fluid communication between the oxygen source and the sensing region;
   a primary heater disposed on the fifth layer for generating heat to maintain the substrate at a temperature less than the first and second operating temperatures;
   a compensation heater disposed on the third layer for generating heat to maintain the first and second catalyst at the first and second substantially constant operating temperature, respectively; and
   an electrical ground plane disposed on the fourth layer for electrically isolating the primary heater from the compensation heater.

34. The differential calorimetric sensor of claim 33 wherein the compensation heater further comprises:
   a first compensation heater on the third layer below the first catalyst for maintaining the first catalyst at the first substantially constant operating temperature; and
   a second compensation heater disposed on the third layer below the second catalyst for maintaining the second catalyst at the second substantially constant operating temperature.

35. The differential calorimetric sensor of claim 33 further comprising:
   a sixth layer positioned adjacent to the fifth layer and having at least one via formed therethrough such that the at least one via of the first, second, third fourth, fifth and sixth layers are aligned to provide fluid communication between the oxygen source and the sensing region;
   a second primary heater disposed on the sixth layer for generating heat to maintain the substrate at a temperature less than the first and second operating temperatures.

36. A differential calorimetric hydrocarbon gas sensor for determining the concentration of hydrocarbon gas species in an gas flow comprising:
   a sensing element located within a sensing region and including a catalytic layer having a first catalyst and a second catalyst disposed on the catalytic layer, the second catalyst having a reference region and comprising a selective combustible catalyst having an active metal component selected from the group consisting of: rhodium, bismuth, palladium, platinum and combinations thereof;
   temperature compensation circuitry operable to generate a sufficient quantity of heat for maintaining the first catalyst at a first substantially constant operating temperature and the second catalyst at a second substantially constant operating temperature;
   temperature reference circuitry operable to measure the sufficient quantity of heat generated by the temperature compensation circuitry;
   a diffusion barrier overlying the catalytic layer for controlling the rate at which the gas diffuses to the catalytic layer and for protecting the catalytic layer from scouring by the gas flow;
   a transport layer interposed between the diffusion barrier and the catalytic layer for further controlling the rate at which the gas flow diffuses to the catalytic layer;
   an oxygen source, the oxygen source and the sensing region being disposed on a region of the sensor that is commonly heated; and
   whereby the concentration of hydrocarbon species in a gas flow can be determined from the sufficient quantity of heat generated by the temperature compensation circuitry and measured by the temperature reference circuitry.

37. The differential calorimetric sensor of claim 36 wherein the reference region comprises a selective combustible catalyst having an active metal component selected from the group consisting of: rhodium, bismuth and combinations thereof.

38. The differential calorimetric sensor of claim 36 wherein the reference region comprises a selective combustible catalyst having an active metal component including a combination of rhodium and bismuth.

39. The differential calorimetric sensor of claim 36 wherein the first catalyst has an active region which accelerates the oxidization of substantially all residual combustible gases present in the gas flow, and the second catalyst reference region selectively accelerates the oxidization of carbon monoxide and hydrogen present in the gas flow.

40. The differential calorimetric sensor of claim 36 wherein the active region comprises a total combustible catalyst having an active metal component selected from the group consisting of: platinum, rhodium, palladium, iridium, ruthenium, and combinations thereof.

41. The differential calorimetric sensor of claim 36 wherein the active region comprises a total combustible catalyst having an active metal component selected from the group consisting of: platinum, rhodium, palladium and combinations thereof.

42. The differential calorimetric sensor of claim 36 wherein the active region comprises a total combustible catalyst having an active metal component including a combination of platinum and rhodium.

43. The differential calorimetric sensor of claim 36 wherein the active region comprises a total combustible catalyst having an active metal component supported on a stable refractory support selected from the group consisting of: alumina, zirconia, titania, silica, silica alumina and combinations thereof.

44. The differential calorimetric sensor of claim 43 wherein the refractory support includes an oxygen storage material.

45. The differential calorimetric sensor of claim 44 wherein the oxygen storage material includes ceria.

46. The differential calorimetric sensor of claim 36 wherein the active region comprises a total combustible catalyst having an active metal component supported on a high surface area, stable refractory support including gamma alumina.

47. The differential calorimetric sensor of claim 46 wherein the refractory support includes an oxygen storage material.

48. The differential calorimetric sensor of claim 47 wherein the oxygen storage material includes ceria.

49. The differential calorimetric sensor of claim 36 wherein the active region comprises a total combustible catalyst having an active metal component supported on a refractory support including a combination of precalcined alumina and ceria stabilized zirconia.

50. The differential calorimetric sensor of claim 36 wherein the active region comprises a total combustible catalyst selected from the group consisting of: platinum and rhodium on prestabilized alumina, platinum and rhodium on ceria alumina, and rhodium on stabilized ceria zirconia.

51. The differential calorimetric sensor of claim 50 wherein the active metal component comprises a combination of rhodium and bismuth having an atomic ratio in the range of 0.5–3.0.

52. The differential calorimetric sensor of claim 51 wherein the active metal component comprises a combination of rhodium and bismuth having an atomic ratio in the range of 1.0–2.5.

53. The differential calorimetric sensor of claim 52 wherein the rhodium and bismuth are combined as a solution of soluble salts.

54. The differential calorimetric sensor of claim 36 wherein the reference region comprises a selective combustible catalyst having an active metal component supported on a stable refractory support selected from the group consisting of: alumina, zirconia, and combinations thereof.

55. The differential calorimetric sensor of claim 54 wherein the refractory support includes an oxygen storage material.

56. The differential calorimetric sensor of claim 55 wherein the oxygen storage material includes ceria.

57. The differential calorimetric sensor of claim 56 wherein the refractory support includes ceria stabilized zirconia.

58. The differential calorimetric sensor of claim 36 wherein the reference region comprises a CO selective catalyst selected from the group consisting of: rhodium and bismuth on ceria zirconia, rhodium and bismuth on zirconia, rhodium and bismuth on alumina, rhodium and bismuth oxide on ceria zirconia, rhodium and bismuth from frit, platinum and bismuth on ceria zirconia, and palladium and bismuth on ceria zirconia.

59. The differential calorimetric sensor of claim 36 wherein the sensing region is supported on a substrate and the oxygen source comprises an electrochemical oxygen source disposed on an opposite side of the substrate.

60. The differential calorimetric sensor of claim 59 wherein the electrochemical oxygen source further comprises:
   an first electrode disposed in spaced relation to the substrate such that an oxygen storage region is formed therebetween;
   an electrolytic layer disposed adjacent the first electrode opposite the oxygen storage region;
   a second electrode disposed adjacent to the electrolytic layer; and
   at least one via formed in the substrate in communication with the oxygen storage region.

61. The differential calorimetric sensor of claim 60 wherein the first and second electrodes are porous platinum electrodes and the electrolytic layer is yttrium stabilized zirconia.

62. The differential calorimetric sensor of claim 61 further comprising a porous protective layer overlying the oxygen source.

63. The differential calorimetric sensor of claim 36 further comprising a substrate including:
   a first layer having the catalytic layer disposed thereon;
   a second layer positioned adjacent to the first layer and having the temperature reference circuitry disposed thereon;
   a third layer positioned adjacent to the second layer and having the temperature compensation circuitry disposed thereon;
   an oxygen source positioned adjacent to the third layer; and
   the first, second and third layers having at least one via formed therethrough to provide fluid communication between the oxygen source and the sensing region.

64. The differential calorimetric sensor of claim 63 wherein the temperature reference circuitry further comprises:
   a first temperature-sensitive element disposed on the second layer below the first catalyst for measuring the temperature of the first catalyst; and
   a second temperature-sensitive element disposed on the second layer below the second catalyst for measuring the temperature of the second catalyst.

65. The differential calorimetric sensor of claim 64 wherein the first temperature-sensitive element and the second temperature-sensitive element are resistive temperature devices.

66. The differential calorimetric sensor of claim 64 wherein the temperature compensation circuitry further comprises:
   a first heat-generating element disposed on the third layer below the first catalyst for maintaining the first catalyst at the first substantially constant operating temperature; and
   a second heat-generating element disposed on the third layer below the second catalyst for maintaining the second catalyst at the second substantially constant operating temperature.

67. The differential calorimetric sensor of claim 66 wherein the first heat-generating element and the second heat-generating element are resistance-based heating elements.

68. The differential calorimetric sensor of claim 64 further comprising:
   a fourth layer positioned adjacent to the third layer;
   a fifth layer positioned adjacent to the fourth layer;
   the fourth and fifth layers having at least one via formed therethrough and aligned with the at least one via of the first, second and third layers to provide fluid communication between the oxygen source and the sensing region;
   a primary heater disposed on the fifth layer for generating heat to maintain the substrate at a temperature less than the first and second operating temperatures;
   a compensation heater disposed on the third layer for generating heat to maintain the first and second catalyst at the first and second substantially constant operating temperature, respectively; and
   an electrical ground plane disposed on the fourth layer for electrically isolating the primary heater from the compensation heater.

69. The differential calorimetric sensor of claim 68 wherein the compensation heater further comprises:
   a first compensation heater on the third layer below the first catalyst for maintaining the first catalyst at the first substantially constant operating temperature; and
   a second compensation heater disposed on the third layer below the second catalyst for maintaining the second catalyst at the second substantially constant operating temperature.

70. The differential calorimetric sensor of claim 68 further comprising:

a sixth layer positioned adjacent to the fifth layer and having at least one via formed therethrough such that the at least one via of the first, second, third fourth, fifth and sixth layers are aligned to provide fluid communication between the oxygen source and the sensing region;

a second primary heater disposed on the sixth layer for generating heat to maintain the substrate at a temperature less than the first and second operating temperatures.

71. A differential calorimetric hydrocarbon gas sensor for determining the concentration of hydrocarbon gas species in a gas flow comprising:

a sensing element located within a sensing region and including a catalytic layer having a first catalyst and a second catalyst disposed on the catalytic layer, the first catalyst having an active region which accelerates the oxidization of substantially all residual combustible gases present in the gas flow, and the second catalyst having a reference region which selectively accelerates the oxidization of carbon monoxide and hydrogen present in the gas flow;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry; and an oxygen source, the oxygen source and the sensing region being disposed on a region of the sensor that is commonly heated, and the oxygen source operable to provide a supply of oxygen to the sensing region;

whereby the concentration of hydrocarbon species in a gas flow can be determined from the sufficient quantity of heat generated by the temperature compensation circuitry and measured by the temperature reference circuitry.

72. The differential calorimetric sensor of claim 71 wherein the sensing region is supported on a substrate and the oxygen source comprises an electrochemical oxygen source disposed on an opposite side of the substrate.

73. The differential calorimetric sensor of claim 72 wherein the electrochemical oxygen source further comprises:

an first electrode disposed in spaced relation to the substrate such that an oxygen storage region is formed therebetween;

an electrolytic layer disposed adjacent the first electrode opposite the oxygen storage region;

a second electrode disposed adjacent to the electrolytic layer; and at least one via formed in the substrate in communication with the oxygen storage region.

74. The differential calorimetric sensor of claim 73 wherein the first and second electrodes are porous platinum electrodes and the electrolytic layer is yttrium stabilized zirconia.

75. The differential calorimetric sensor of claim 72 further comprising a porous protective layer overlying the oxygen source.

76. The differential calorimetric sensor of claim 72 wherein the substrate comprises:

a first layer having the catalytic layer disposed thereon;

a second layer positioned adjacent to the first layer and having the temperature reference circuitry disposed thereon;

a third layer positioned adjacent to the second layer and having the temperature compensation circuitry disposed thereon;

the oxygen source positioned adjacent to the third layer; and the first, second and third layers having at least one via formed therethrough to provide fluid communication between the oxygen source and the sensing region.

77. The differential calorimetric sensor of claim 76 wherein the temperature compensation circuitry further comprises:

a first heat-generating element disposed on the third layer below the first catalyst for maintaining the first catalyst at the first substantially constant operating temperature; and a second heat-generating element disposed on the third layer below the second catalyst for maintaining the second catalyst at the second substantially constant operating temperature.

78. The differential calorimetric sensor of claim 77 wherein the first heat-generating element and the second heat-generating element are resistance-based heating elements.

79. The differential calorimetric sensor of claim 76 further comprising:

a fourth layer positioned adjacent to the third layer;

a fifth layer positioned adjacent to the fourth layer;

the fourth and fifth layers having at least one via formed therethrough and aligned with the at least one via of the first, second and third layers to provide fluid communication between the oxygen source and the sensing region;

a primary heater disposed on the fifth layer for generating heat to maintain the substrate at a temperature less than the first and second operating temperatures;

a compensation heater disposed on the third layer for generating heat to maintain the first and second catalyst at the first and second substantially constant operating temperature, respectively; and an electrical ground plane disposed on the fourth layer for electrically isolating the primary heater from the compensation heater.

80. The differential calorimetric sensor of claim 79 further comprising:

a sixth layer positioned adjacent to the fifth layer and having at least one via formed therethrough such that the at least one via of the first, second, third fourth, fifth and sixth layers are aligned to provide fluid communication between the oxygen source and the sensing region;

a second primary heater disposed on the sixth layer for generating heat to maintain the substrate at a temperature less than the first and second operating temperatures.

81. The differential calorimetric sensor of claim 72 further comprising an oxygen sensor cell.

82. The differential calorimetric sensor of claim 81 wherein the oxygen sensor cell is operable in either of a potentiometric mode and a driven mode.

83. The differential calorimetric sensor of claim 81 wherein the electrochemical oxygen source further comprises:

an first electrode disposed in spaced relation to the substrate such that an oxygen storage region is formed therebetween;

an electrolytic layer disposed adjacent the first electrode opposite the oxygen storage region;

a second electrode disposed adjacent to the electrolytic layer;

at least one via formed in the substrate in communication with the oxygen storage region;

and the oxygen sensor cell comprises:

a third electrode disposed adjacent the oxygen storage region and the electrolyte layer; and a fourth electrode disposed adjacent the electrolyte layer and opposite the oxygen storage region.

84. A differential calorimetric hydrocarbon gas sensor for determining the concentration of hydrocarbon gas species in a gas flow comprising:

a first calorimeter including a first catalyst, the first catalyst having an active region comprising a total combustible catalyst having an active metal component selected form the group consisting of: platinum, rhodium, palladium, iridium, ruthenium, and combinations thereof, disposed on a first layer and in fluid communication with a sensing region a first temperature-sensitive element disposed on a second layer adjacent the first layer, and a first compensation heater disposed on a third layer adjacent the second layer, the first compensation heater operable to generate a sufficient quantity of heat for maintaining the first catalyst at a first substantially constant operating temperature;

a second calorimeter including a second catalyst, the second catalyst having a reference region comprising a selective combustible catalyst having an active metal component selected from the group consisting of: rhodium, bismuth, palladium, platinum and combinations thereof, disposed on the first layer and in fluid communication with the sensing region, a second temperature-sensitive element disposed on the second layer, and a second compensation heater disposed on the third layer, the second compensation heater operable to generate a sufficient quantity of heat for maintaining the second catalyst at a second substantially constant operating temperature; and control circuitry operable to compute a difference between the power output of the first compensation heater and the second compensation heater, whereby the concentration of hydrocarbon gas species in a gas flow is determined from the difference.

85. The differential calorimetric sensor of claim 84 further comprising:

a primary heater disposed on a fourth layer such that the primary heater is nominally symmetrically positioned with respect to the first and second calorimeters;

the primary heater and the first compensation heater operable to generate heat to maintain the first catalytic layer at the first substantially constant operating temperature; and the primary heater and the second compensation heater operable to generate heat to maintain the second catalytic layer at the second substantially constant operating temperature.

86. The differential calorimetric sensor of claim 85 further comprising primary heater control circuitry operable to maintain the second calorimeter within a specified temperature range, the specified temperature range being less than the first and second substantially constant operating temperatures.

87. The differential calorimetric hydrocarbon gas sensor of claim 86 further comprising compensation heater control circuitry operable to control the first compensation heater for maintaining the first calorimeter at the first substantially constant operating temperature and further operable to control the second compensation heater for maintaining the second calorimeter at the second substantially constant operating temperature.

88. The differential calorimetric hydrocarbon gas sensor of claim 84 further comprising reference power equalization circuitry operable to maintain a first power input to the first compensation heater at a first level and further operable to maintain a second power input to the second compensation heater at a second level.

89. The differential calorimetric hydrocarbon gas sensor of claim 84 further comprising response equalization circuitry operable to minimize difference between the response of the first temperature-sensitive element and the response of the second temperature-sensitive element.

90. A differential calorimetric hydrocarbon gas sensor for determining the concentration of hydrocarbon gas species in an gas flow comprising:

a first layer having the catalytic layer including a first catalyst, the first catalyst having an active region comprising a total combustible catalyst having an active metal component selected form the group consisting of: platinum, rhodium, palladium, iridium, ruthenium, and combinations thereof, and a second catalyst, the second catalyst having a reference region comprising a selective combustible catalyst having an active metal component selected from the group consisting of: rhodium, bismuth, palladium, platinum and combinations thereof, disposed thereon;

a second layer disposed beneath the first layer and having a first temperature-sensitive element disposed on the second layer below the first catalyst for measuring the temperature of the first catalyst, and a second temperature-sensitive element disposed on the second layer below the second catalyst for measuring the temperature of the second catalyst;

a third layer disposed beneath the second layer and having a first compensation heater disposed on the third layer below the first catalyst for maintaining the first catalyst at a first substantially constant operating temperature, and a second compensation heater disposed on the third layer below the second catalyst for maintaining the second catalyst at a second substantially constant operating temperature;

a fourth layer disposed beneath the third layer and having a electrical ground plane disposed thereon;

a fifth layer disposed beneath the fourth layer and having a first primary heater disposed thereon;

a sixth layer disposed beneath the fifth layer and having a second primary heater disposed thereon, the first and second primary heaters operable for generating heat to maintain the substrate at a temperature less than the first and second substantially constant operating temperatures;

an electrochemical oxygen source disposed beneath the sixth layer and having an first electrode disposed in spaced relation to the sixth layer such that an oxygen storage region is formed therebetween, an electrolytic layer disposed beneath the first electrode opposite the oxygen storage region, and a second electrode disposed beneath to the electrolytic layer;

a porous protective layer overlying the electrochemical oxygen source for protecting the electrochemical pump from scouring by the gas flow;

a diffusion barrier overlying the catalytic layer in spaced relation to form a transport layer therebetween, the diffusion barrier for controlling the rate at which the gas flow diffuses to the catalytic layer and for protecting the catalytic layer from scouring by the gas flow; and at least one via formed through the first, second, third fourth, fifth and sixth layers to provide fluid communication between the oxygen storage region and the sensing region.

91. A differential calorimetric gas sensor for use in an exhaust gas flow comprising:

a first sensing element for determining the concentration of hydrocarbon gas species present within a first sensing region, the first sensing element including a catalytic layer having a first catalyst and a second catalyst disposed on the catalytic layer, the first catalyst and the second catalyst differing in their catalytic activity for oxidation of hydrocarbon gas species;

temperature compensation circuitry operable to maintain the first catalyst at a first substantially constant operating temperature and the second catalyst at a second substantially constant operating temperature;

temperature reference circuitry operable to measure the heat generated by the temperature compensation circuitry to maintain the first and second substantially constant operating temperature of the first catalyst and the second catalyst;

an oxygen source operable to provide a supply of oxygen to the sensing region and disposed within a region of the sensor in thermal communication with the temperature compensation circuitry to be maintained at the first operating temperature; and a second sensing element for determining the concentration of oxygen present within a second sensing region, the second sensing element including a reference electrode operable to measure the oxygen concentration in the supply of oxygen and an exhaust gas electrode operable to measure the oxygen concentration in the second sensing region.

92. The differential calorimetric sensor of claim 91 wherein the second sensing element is operable in either of a potentiometric mode and a driven mode to measure oxygen concentration in the supply of oxygen.

93. The differential calorimetric sensor of claim 91 further comprising:

a first layer having the catalytic layer disposed thereon;

a second layer positioned adjacent to the first layer and having the temperature reference circuitry disposed thereon;

a third layer positioned adjacent to the second layer and having the temperature compensation circuitry disposed thereon;

the oxygen source positioned adjacent to the third layer and comprising:

a first electrode disposed in spaced relation to the third layer such that an oxygen storage region is formed therebetween;

an electrolytic layer disposed adjacent the first electrode opposite the oxygen storage region;

a second electrode disposed adjacent to the electrolytic layer;

a third electrode disposed adjacent to and electrically isolated from the first electrode in the oxygen storage region; and a fourth electrode disposed adjacent to and electrically isolated from the second electrode.

94. The differential calorimetric sensor of claim 93 wherein the first, second, third and fourth electrodes are porous platinum electrodes and the electrolytic layer is yttrium stabilized zirconia.

95. A differential calorimetric hydrocarbon gas sensor for determining the concentration of hydrocarbon gas species in a gas flow comprising:

a sensing element located within a sensing region and including a catalytic layer having a first catalyst and a second catalyst disposed on the catalytic layer, the first catalyst having an active region comprising a total combustible catalyst having an active metal component selected form the group consisting of: platinum, rhodium, palladium, iridium, ruthenium, and combinations thereof, and the second catalyst differing from the first catalyst in its catalytic activity for oxidation of hydrocarbons and comprising a selective combustible catalyst having an active metal component including a combination of rhodium and bismuth;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry; and whereby the concentration of hydrocarbon species in a gas flow can be determined from the sufficient quantity of heat generated by the temperature compensation circuitry and measured by the temperature reference circuitry.

96. The differential calorimetric sensor of claim 95 wherein the active metal component comprises a combination of rhodium and bismuth having an atomic ratio in the range of 0.5–3.0.

97. The differential calorimetric sensor of claim 96 wherein the active metal component comprises a combination of rhodium and bismuth having an atomic ratio in the range of 1.0–2.5.

98. The differential calorimetric sensor of claim 95 wherein the rhodium and bismuth are combined as a solution of soluble salts.

99. A differential calorimetric hydrocarbon gas sensor for determining the concentration of hydrocarbon gas species in a gas flow comprising:

a sensing element located within a sensing region and including a catalytic layer having a first catalyst and a second catalyst disposed on the catalytic layer, the first catalyst having an active region comprising a total combustible catalyst having an active metal component selected form the group consisting of: platinum, rhodium, palladium, iridium, ruthenium, and combinations thereof, and the second catalyst differing from the first catalyst in its catalytic activity for oxidation of hydrocarbons and comprising a CO selective catalyst selected from the group consisting of: rhodium and bismuth on ceria zirconia, rhodium and bismuth on zirconia, rhodium and bismuth on alumina, rhodium and bismuth on ceria zirconia, rhodium and bismuth from frit, platinum and bismuth on ceria zirconia, and palladium and bismuth on ceria zirconia;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry; and whereby the concentration of hydrocarbon species in a gas flow can be determined from the sufficient quantity of heat generated by the temperature compensation circuitry and measured by the temperature reference circuitry.

100. A differential calorimetric hydrocarbon gas sensor for determining the concentration of hydrocarbon gas species in a gas flow comprising:

a sensing element located within a sensing region and including a catalytic layer having a first catalyst and a second catalyst disposed on the catalytic layer, the first catalyst having an active region comprising a total combustible catalyst having an active metal component selected form the group consisting of: platinum, rhodium, palladium, iridium, ruthenium, and combinations thereof, and the second catalyst differing from the first catalyst in its catalytic activity for oxidation of hydrocarbons and comprising a selective combustible catalyst having an active metal component including a combination of rhodium and bismuth;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry;

a substrate including:
  a first layer having the catalytic layer disposed thereon;
  a second layer positioned adjacent to the first layer and having the temperature reference circuitry disposed thereon;
  a third layer positioned adjacent to the second layer and having the temperature compensation circuitry disposed thereon;
  an oxygen source positioned adjacent to the third layer;
  the first, second and third layers having at least one via formed therethrough to provide fluid communication between the oxygen source and the sensing region; and
  whereby the concentration of hydrocarbon species in a gas flow can be determined from the sufficient quantity of heat generated by the temperature compensation circuitry and measured by the temperature reference circuitry.

101. The differential calorimetric sensor of claim 100 wherein the temperature reference circuitry further comprises:

a first temperature-sensitive element disposed on the second layer below the first catalyst for measuring the temperature of the first catalyst; and a second temperature-sensitive element disposed on the second layer below the second catalyst for measuring the temperature of the second catalyst.

102. The differential calorimetric sensor of claim 101 wherein the first temperature-sensitive element and the second temperature-sensitive element are resistive temperature devices.

103. The differential calorimetric sensor of claim 101 wherein the temperature compensation circuitry further comprises:

a first heat-generating element disposed on the third layer below the first catalyst for maintaining the first catalyst at the first substantially constant operating temperature; and a second heat-generating element disposed on the third layer below the second catalyst for maintaining the second catalyst at the second substantially constant operating temperature.

104. The differential calorimetric sensor of claim 103 wherein the first heat-generating element and the second heat-generating element are resistance-based heating elements.

105. The differential calorimetric sensor of claim 101 further comprising:

a fourth layer positioned adjacent to the third layer;

a fifth layer positioned adjacent to the fourth layer;

the fourth and fifth layers having at least one via formed therethrough and aligned with the at least one via of the first, second and third layers to provide fluid communication between the oxygen source and the sensing region;

a primary heater disposed on the fifth layer for generating heat to maintain the substrate at a temperature less than the first and second operating temperatures;

a compensation heater disposed on the third layer for generating heat to maintain the first and second catalyst at the first and second substantially constant operating temperature, respectively; and an electrical ground plane disposed on the fourth layer for electrically isolating the primary heater from the compensation heater.

106. The differential calorimetric sensor of claim 105 wherein the compensation heater further comprises:

a first compensation heater on the third layer below the first catalyst for maintaining the first catalyst at the first substantially constant operating temperature; and a second compensation heater disposed on the third layer below the second catalyst for maintaining the second catalyst at the second substantially constant operating temperature.

107. The differential calorimetric sensor of claim 105 further comprising:

a sixth layer positioned adjacent to the fifth layer and having at least one via formed therethrough such that the at least one via of the first, second, third fourth, fifth and sixth layers are aligned to provide fluid communication between the oxygen source and the sensing region;

a second primary heater disposed on the sixth layer for generating heat to maintain the substrate at a temperature less than the first and second operating temperatures.

108. A differential calorimetric hydrocarbon gas sensor for determining the concentration of hydrocarbon gas species in an gas flow comprising:

a sensing element located within a sensing region and including a catalytic layer having a first catalyst and a second catalyst disposed on the catalytic layer, the second catalyst having a reference region and comprising a selective combustible catalyst having an active metal component including a combination of rhodium and bismuth;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry; and whereby the concentration of hydrocarbon species in a gas flow can be determined from the sufficient quantity of heat generated by the temperature compensation circuitry and measured by the temperature reference circuitry.

109. A differential calorimetric hydrocarbon gas sensor for determining the concentration of hydrocarbon gas species in an gas flow comprising:

a sensing element located within a sensing region and including a catalytic layer having a first catalyst and a second catalyst disposed on the catalytic layer, the second catalyst having a reference region and comprising a selective combustible catalyst having an active metal component selected from the group consisting of: rhodium, bismuth, palladium, platinum and combinations thereof;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry;

a substrate including:
a first layer having the catalytic layer disposed thereon;
a second layer positioned adjacent to the first layer and having the temperature reference circuitry disposed thereon;
a third layer positioned adjacent to the second layer and having the temperature compensation circuitry disposed thereon;
an oxygen source positioned adjacent to the third layer;
the first, second and third layers having at least one via formed therethrough to provide fluid communication between the oxygen source and the sensing region; and whereby the concentration of hydrocarbon species in a gas flow can be determined from the sufficient quantity of heat generated by the temperature compensation circuitry and measured by the temperature reference circuitry.

110. The differential calorimetric sensor of claim 109 wherein the temperature reference circuitry further comprises:

a first temperature-sensitive element disposed on the second layer below the first catalyst for measuring the temperature of the first catalyst; and a second temperature-sensitive element disposed on the second layer below the second catalyst for measuring the temperature of the second catalyst.

111. The differential calorimetric sensor of claim 110 wherein the first temperature-sensitive element and the second temperature-sensitive element are resistive temperature devices.

112. The differential calorimetric sensor of claim 111 wherein the temperature compensation circuitry further comprises:

a first heat-generating element disposed on the third layer below the first catalyst for maintaining the first catalyst at the first substantially constant operating temperature; and a second heat-generating element disposed on the third layer below the second catalyst for maintaining the second catalyst at the second substantially constant operating temperature.

113. The differential calorimetric sensor of claim 112 wherein the first heat-generating element and the second heat-generating element are resistance-based heating elements.

114. The differential calorimetric sensor of claim 110 further comprising:

a fourth layer positioned adjacent to the third layer;
a fifth layer positioned adjacent to the fourth layer;
the fourth and fifth layers having at least one via formed therethrough and aligned with the at least one via of the first, second and third layers to provide fluid communication between the oxygen source and the sensing region;

a primary heater disposed on the fifth layer for generating heat to maintain the substrate at a temperature less than the first and second operating temperatures;

a compensation heater disposed on the third layer for generating heat to maintain the first and second catalyst at the first and second substantially constant operating temperature, respectively; and an electrical ground plane disposed on the fourth layer for electrically isolating the primary heater from the compensation heater.

115. The differential calorimetric sensor of claim 114 wherein the compensation heater further comprises:

a first compensation heater on the third layer below the first catalyst for maintaining the first catalyst at the first substantially constant operating temperature; and a second compensation heater disposed on the third layer below the second catalyst for maintaining the second catalyst at the second substantially constant operating temperature.

116. The differential calorimetric sensor of claim 114 further comprising:

a sixth layer positioned adjacent to the fifth layer and having at least one via formed therethrough such that the at least one via of the first, second, third fourth, fifth and sixth layers are aligned to provide fluid communication between the oxygen source and the sensing region;

a second primary heater disposed on the sixth layer for generating heat to maintain the substrate at a temperature less than the first and second operating temperatures.

117. A differential calorimetric hydrocarbon gas sensor for determining the concentration of hydrocarbon gas species in a gas flow comprising:

a sensing element located within a sensing region supported on a substrate and including a catalytic layer having a first catalyst and a second catalyst disposed on the catalytic layer, the first catalyst having an active region which accelerates the oxidization of substantially all residual combustible gases present in the gas flow, and the second catalyst having a reference region which selectively accelerates the oxidization of carbon monoxide and hydrogen present in the gas flow;

temperature compensation circuitry operable to generate a sufficient quantity of heat for maintaining the first catalyst at a first substantially constant operating temperature and the second catalyst at a second substantially constant operating temperature;

temperature reference circuitry operable to measure the sufficient quantity of heat generated by the temperature compensation circuitry;

an oxygen source disposed on an opposite side of the substrate than the sensing region and being operable to provide a supply of oxygen to the sensing region;

wherein the substrate comprises:
 a first layer having the catalytic layer disposed thereon;
 a second layer positioned adjacent to the first layer and having the temperature reference circuitry disposed thereon;
 a third layer positioned adjacent to the second layer and having the temperature compensation circuitry disposed thereon;
 the oxygen source positioned adjacent to the third layer; and
 the first, second and third layers having at least one via formed therethrough to provide fluid communication between the oxygen source and the sensing region; and
 whereby the concentration of hydrocarbon species in a gas flow can be determined from the sufficient quantity of heat generated by the temperature compensation circuitry and measured by the temperature reference circuitry.

118. The differential calorimetric sensor of claim 117 wherein the temperature compensation circuitry further comprises:
 a first heat-generating element disposed on the third layer below the first catalyst for maintaining the first catalyst at the first substantially constant operating temperature; and
 a second heat-generating element disposed on the third layer below the second catalyst for maintaining the second catalyst at the second substantially constant operating temperature.

119. The differential calorimetric sensor of claim 118 wherein the first heat-generating element and the second heat-generating element are resistance-based heating elements.

120. The differential calorimetric sensor of claim 118 further comprising:
 a fourth layer positioned adjacent to the third layer;
 a fifth layer positioned adjacent to the fourth layer;
 the fourth and fifth layers having at least one via formed therethrough and aligned with the at least one via of the first, second and third layers to provide fluid communication between the oxygen source and the sensing region;
 a primary heater disposed on the fifth layer for generating heat to maintain the substrate at a temperature less than the first and second operating temperatures;
 a compensation heater disposed on the third layer for generating heat to maintain the first and second catalyst at the first and second substantially constant operating temperature, respectively; and
 an electrical ground plane disposed on the fourth layer for electrically isolating the primary heater from the compensation heater.

121. The differential calorimetric sensor of claim 120 further comprising:
 a sixth layer positioned adjacent to the fifth layer and having at least one via formed therethrough such that the at least one via of the first, second, third fourth, fifth and sixth layers are aligned to provide fluid communication between the oxygen source and the sensing region;
 a second primary heater disposed on the sixth layer for generating heat to maintain the substrate at a temperature less than the first and second operating temperatures.

122. A differential calorimetric hydrocarbon gas sensor for determining the concentration of hydrocarbon gas species in a gas flow comprising:
 a sensing element located within a sensing region supported on a substrate and including a catalytic layer having a first catalyst and a second catalyst disposed on the catalytic layer, the first catalyst having an active region which accelerates the oxidization of substantially all residual combustible gases present in the gas flow, and the second catalyst having a reference region which selectively accelerates the oxidization of carbon monoxide and hydrogen present in the gas flow;
 temperature compensation circuitry operable to generate a sufficient quantity of heat for maintaining the first catalyst at a first substantially constant operating temperature and the second catalyst at a second substantially constant operating temperature;
 temperature reference circuitry operable to measure the sufficient quantity of heat generated by the temperature compensation circuitry;
 an oxygen source disposed on an opposite side of the substrate than the sensing region and being operable to provide a supply of oxygen to the sensing region;
 an oxygen sensor cell;
 wherein the electrochemical oxygen source further comprises:
  an first electrode disposed in spaced relation to the substrate such that an oxygen storage region is formed therebetween;
  an electrolytic layer disposed adjacent the first electrode opposite the oxygen storage region;
  a second electrode disposed adjacent to the electrolytic layer;
  at least one via formed in the substrate in communication with the oxygen storage region;
 and the oxygen sensor cell comprises:
  a third electrode disposed adjacent the oxygen storage region and the electrolyte layer; and
  a fourth electrode disposed adjacent the electrolyte layer and opposite the oxygen storage region; and
  whereby the concentration of hydrocarbon species in a gas flow can be determined from the sufficient quantity of heat generated by the temperature compensation circuitry and measured by the temperature reference circuitry.

123. A differential calorimetric gas sensor for use in an exhaust gas flow comprising:
 a first sensing element for determining the concentration of hydrocarbon gas species present within a first sensing region, the first sensing element including a catalytic layer having a first catalyst and a second catalyst disposed on the catalytic layer, the first catalyst and the second catalyst differing in their catalytic activity for oxidation of hydrocarbon gas species;
 temperature compensation circuitry operable to maintain the first catalyst at a first substantially constant operating temperature and the second catalyst at a second substantially constant operating temperature;

temperature reference circuitry operable to measure the heat generated by the temperature compensation circuitry to maintain the first and second substantially constant operating temperature of the first catalyst and the second catalyst;

an oxygen source operable to provide a supply of oxygen to the sensing region;

a second sensing element for determining the concentration of oxygen present within a second sensing region, the second sensing element including a reference electrode operable to measure the oxygen concentration in the supply of oxygen and an exhaust gas electrode operable to measure the oxygen concentration in the second sensing region;

a first layer having the catalytic layer disposed thereon;

a second layer positioned adjacent to the first layer and having the temperature reference circuitry disposed thereon;

a third layer positioned adjacent to the second layer and having the temperature compensation circuitry disposed thereon;

the oxygen source positioned adjacent to the third layer and comprising:

a first electrode disposed in spaced relation to the third layer such that an oxygen storage region is formed therebetween;

an electrolytic layer disposed adjacent the first electrode opposite the oxygen storage region;

a second electrode disposed adjacent to the electrolytic layer;

a third electrode disposed adjacent to and electrically isolated from the first electrode in the oxygen storage region; and a fourth electrode disposed adjacent to and electrically isolated from the second electrode.

124. The differential calorimetric sensor of claim 123 wherein the first, second, third and fourth electrodes are porous platinum electrodes and the electrolytic layer is yttrium stabilized zirconia.

* * * * *